(12) United States Patent
Wang

(10) Patent No.: US 8,835,643 B2
(45) Date of Patent: Sep. 16, 2014

(54) MOLECULES, COMPOSITIONS, AND METHODS FOR LIGHT ABSORPTION

(75) Inventor: Jinye Wang, Shanghai (CN)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/878,947

(22) PCT Filed: Feb. 23, 2012

(86) PCT No.: PCT/CN2012/071501
§ 371 (c)(1),
(2), (4) Date: Apr. 11, 2013

(87) PCT Pub. No.: WO2013/123658
PCT Pub. Date: Aug. 29, 2013

(65) Prior Publication Data
US 2014/0193348 A1 Jul. 10, 2014

(51) Int. Cl.
 *C07D 213/04* (2006.01)
 *A61K 8/63* (2006.01)
 *A61Q 17/04* (2006.01)

(52) U.S. Cl.
CPC . *A61K 8/63* (2013.01); *A61Q 17/04* (2013.01); *C07D 213/04* (2013.01)
USPC .......................................................... 546/335

(58) Field of Classification Search
CPC .................................................... C07D 213/04
USPC ........................................................ 546/335
See application file for complete search history.

(56) References Cited

U.S. PATENT DOCUMENTS

| | | | |
|---|---|---|---|
| 5,409,502 | A | 4/1995 | Braun |
| 5,609,852 | A | 3/1997 | Galley |
| 5,874,443 | A | 2/1999 | Kiely et al. |
| 5,886,210 | A | 3/1999 | Rayle et al. |
| 5,922,683 | A | 7/1999 | Or et al. |
| 6,350,759 | B1 | 2/2002 | Casara et al. |
| 6,500,825 | B2 | 12/2002 | Lan et al. |
| 6,506,787 | B2 | 1/2003 | Fujishita et al. |
| 6,509,331 | B1 | 1/2003 | Audia et al. |
| 6,531,118 | B1 | 3/2003 | Gonzalez et al. |
| 6,872,243 | B2 | 3/2005 | Breton et al. |
| 2007/0020208 | A1 | 1/2007 | Gutkowski et al. |

FOREIGN PATENT DOCUMENTS

| | | |
|---|---|---|
| CN | 2004/10015929.8 | 1/2004 |
| CN | 03151142.2 | 9/2004 |
| CN | 1557495 | 12/2004 |
| CN | 200610026472.X | 5/2006 |
| CN | 1830968 | 9/2006 |
| CN | 1850844 | 10/2006 |
| DE | 4219738 A | 12/1993 |
| EP | 600045 A | 6/1994 |
| EP | 1 463 513 | 6/2003 |
| JP | 4215360 | 1/2009 |
| WO | WO 93/25182 | 12/1993 |

OTHER PUBLICATIONS

Ju et al. (STN Abstract of: Gaodeng Xuexiao Huaxue Xuebao (2004), 25(12), 2308-2311).*
Bos JD, Meinardi MM, The 500 Dalton rule for the skin penetration of chemical compounds and drugs, Department of Dermatology, Academic Medical Center, University of Amsterdam, The Netherlands Jun. 2000, http://www.ncbi.nlm.nih.gov/pubmed/10839713.
Diffey, B.L. A method for broad spectrum classification of sunscreens. International Journal of Cosmetic Science, 1994. 16, 47-52.
Excimer, Slap-happy azobenzenes, Apr. 20, 2007, p. 36; Handbook of dangerous materials, 1951, and Weisburger, EK—Basic life science, 1983, V24, N23, http://www.coronene.com/blog/?p=110.
International Search Report and Written Opinion received in International Application No. PCT/CN2012/071501, dated Dec. 6, 2012, filed on Feb. 23, 2012.
Jung et al., "Novel Vesicular Aggregates of Crown-Appended Cholesterol Derivatives Which Act as Gelators of Organic Solvents and as Templates for Silica," Journal of the American Chemical Society, 2000, pp. 8648-8653, vol. 122 (36).
Jung et al., "Sol-Gel Polycondensation of Tetraethoxysilane in a Cholesterol-Based Organogel System Results in Chiral Spiral Silica," Angewandte Chemie., International Edition, 2000, pp. 1862-1865, vol. 39 (10).
Loren Pickart, PhD, Skin Biology, The Dangers of Sunscreen Chemicals, http://web.archive.org/web/20120227002707/http://www.reverseskinaging.com/toxicsunscreens2.html; the original document is not available, but Applicant is providing this copy which appears to have been archived on Apr. 30, 2012.
Merino, Estíbaliz', "Synthesis of azobenzenes: the coloured pieces of molecular materials," Chem, Soc. Rev., 2011, 40, 3835-3853.
Moyal, Dominique, "How to Measure UVA Protection Afforded by Sunscreen Products: Critical Wavelength Method". Expert Rev Dermatol. 2008; 3(3): 307-313.
Thune, "Contact and photocontact allergy to suncreens" in Photodermatol. (Feb. 1984;1(1):5-9).

* cited by examiner

*Primary Examiner* — Robert Havlin
(74) *Attorney, Agent, or Firm* — Knobbe, Martens, Olson & Bear, LLP

(57) ABSTRACT

Embodiments provided herein relate to molecules, compositions, and methods for light absorption. In some embodiments, the molecules and/or compositions can be used to absorb ultraviolet light. In some embodiments, the ultraviolet light absorption compound can be used in a sunscreen composition. In some embodiments, the compound includes an azobenzene group for the absorption of ultraviolet light.

9 Claims, 12 Drawing Sheets
(10 of 12 Drawing Sheet(s) Filed in Color)

MOLECULES, COMPOSITIONS, AND METHODS FOR LIGHT ABSORPTION

CROSS-REFERENCE TO RELATED APPLICATIONS

This application is the U.S. National Phase entry under 35 U.S.C. §371 of International Application No. PCT/CN2012/071501, filed Feb. 23, 2012, the contents of which are hereby incorporated by reference in its entirety.

BACKGROUND

While a number of sun screening agents protect from UVB (280-320 nm), there are a growing number that also attempt to protect the skin from UVA (320-400 nm).

SUMMARY

In some embodiments, a molecule is provided. The molecule can include an azobenzene group attached to a heterocycle group and/or a cholesterol group.

In some embodiments, a sunscreen composition is provided. The sunscreen composition can include an azobenzene group. In some embodiments, the azobenzene can be present in an amount that is sufficient to serve as a sunscreen at an SPF of at least 15. In some embodiments, the azobenzene can be present in an amount that is sufficient to serve as a sunscreen and/or UVA protector. In some embodiments, the azobenzene can be present in an amount that is sufficient to serve as a sunscreen for 40 minutes or 80 minutes.

In some embodiments, a pharmaceutical composition is provided. The composition can include any of the molecules provided herein.

In some embodiments, a sunscreen composition is provided. The sunscreen can include an azobenzene attached to at least one of the following: a heterocycle group, a cholesterol group, or both a heterocycle group and a cholesterol group.

In some embodiments, a method of absorbing light is provided. The method can include applying a composition including an azobenzene to a surface, wherein the azobenzene is attached to at least one of the following: a heterocycle group, a cholesterol group, or both a heterocycle group and a cholesterol group. The method can further include exposing the surface to a source of ultraviolet light such that a cis form of the azobenzene is formed, allowing the cis form of the azobenzene to change to a trans form of the azobenzene, and re-exposing the surface to a source of ultraviolet light.

In some embodiments, a method of reactivating (or regenerating) a sunscreen is provided. The method can include providing a sunscreen that includes a trans azobenzene, exposing the trans azobenzene to ultraviolet light for a first period of time to convert the trans azobenzene to a cis azobenzene, and allowing the cis azobenzene to return to the trans azobenzene to form reactivated trans azobenzene to reactivate (or regenerate) the sunscreen.

In some embodiments, a sunscreen is provided. The sunscreen can include a trans form of a molecule having an azobenzene group in an amount that is sufficient to serve as the active ingredient in the sunscreen.

In some embodiments, a method of making a UV absorbing agent is provided. The method can include providing an azo compound and attaching a cholesterol group to the azo compound.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A shows that the integrated area from 290 nm to 400 nm was 137.811, and that its 90% value was 124.030. FIG. 5B shows an integrated area from 290-390 of 125.025. FIG. 5C shows an integrated area from 290-389 of 123.707.

DETAILED DESCRIPTION OF THE PREFERRED EMBODIMENT

Figure 1:
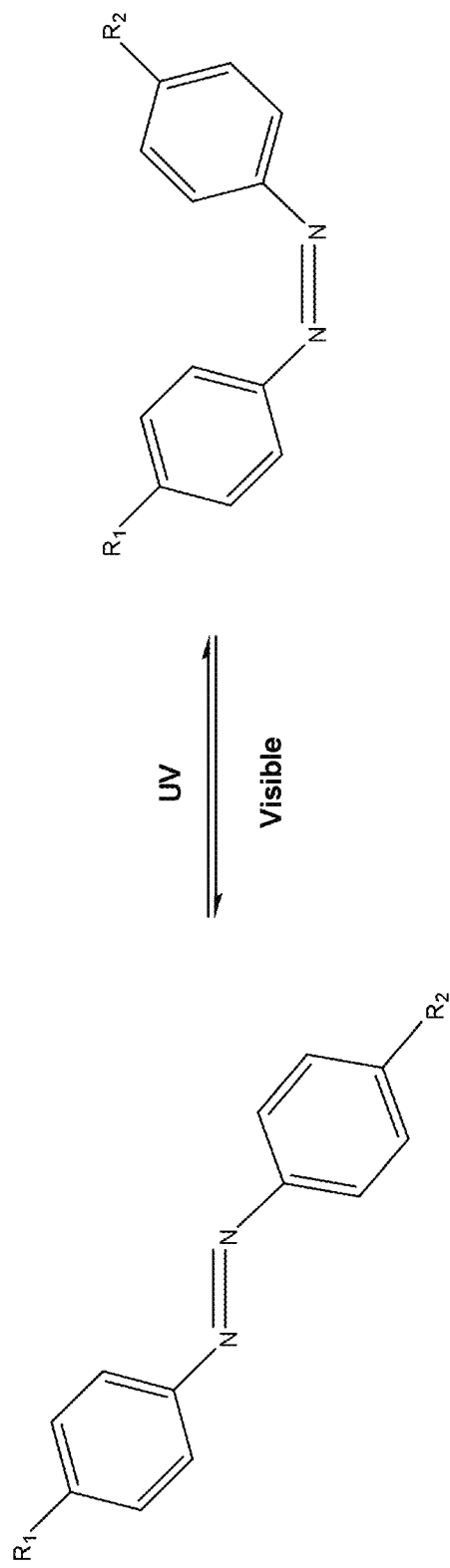
FIG. 1 is a depiction of a reaction scheme of an azobenzene molecule going from trans to cis upon exposure of the trans form to UVA, and from cis to trans, upon exposure of the cis form to visible light, respectively.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It has been appreciated that existing radiation absorbing molecules generally have low absorption efficiency, inferior light stability and/or strong skin irritation. In light of this, a new class of compounds has been identified as having value in protection from one or more of the above and/or UVA.

In some embodiments, one or more of these or other issues can be addressed by using, for example, a molecule that can undergo reversible photo-isomerization. In some embodiments, the molecule can include an azobenzene group. In some embodiments, the molecule can include a cholesterol group. In some embodiments, the molecule can include a heterocycle group. In some embodiments, the molecule can be included in a sunscreen composition. In some embodiments, the molecule is included in a composition in an amount (e.g., at a concentration) that is adequate for the molecule to block a desired amount of UV radiation. In some embodiments, it blocks UVA radiation.

In some embodiments, the azobenzene compounds possess UVA-absorbing property (e.g., UVL or 315 (or 320)-400 nm). In some embodiments, during or after UVA absorption, a trans form of the molecule is isomerized to a cis form. In some embodiments, when exposed to body temperature and visible light (e.g., 400-720), the cis form can return to trans-form, thereby allowing the molecule to absorb more UVA. In some embodiments, one or more of the compounds mentioned herein can be used as sunscreen agents, and can be less photolytic than other compounds. In some embodiments, this property can reduce dosage, application times of the agents, and/or skin discomfort.

The present specification provides a brief section regarding definitions and alternative embodiments. The specification then provides a generic set of embodiments, followed by various sections that provide more detailed options for some of the possible embodiments. The specification then provides a set of Examples.

DEFINITIONS AND EMBODIMENTS

"Benzene" denotes six carbons atoms in a ring. In some embodiments, there is one hydrogen atom attached to each carbon atom. In some embodiments, there are fewer hydrogen atoms than carbon atoms (e.g., 5, 4, 3, 2, 1, or none). Benzene encompasses single benzene structures as well as benzene derivatives, including, for example, bi and tri benzene structures.

The term "critical wavelength method" denotes a method of measuring of the breadth of UVA protection using the "critical wavelength". To obtain this value, the absorbance of the molecule or material is integrated (summed) from 290 nm across the UV wavelengths until the sum reaches 90% of the total absorbance of the sunscreen in the UV region of 290-400 nm. The wavelength where the summed absorbance reaches 90% of the total absorbance is the "critical wavelength". The critical wavelength can be defined by the following equation:

$$\int_{290}^{\lambda_c} lg[1/T(\lambda)]d\lambda = 0.9 \cdot \int_{290}^{400} lg[1/T(\lambda)]d\lambda$$

In some embodiments, the sunscreen will have a λc of at least 370 nm, e.g., 371, 372, 373, 374, 375, 376, 378, 379, 380, 381, 382, 383, 384, 385, 386, 387, 388, 389, 390, 391, 392, 393, 394, 395, 396, 397, 398, 399 or greater, including any range defined between any two of the preceding values and any range above or below any one of the preceding values.

"Azo" compounds are compounds bearing the functional group R—N=N—R'. In some embodiments, R and R' can be either aryl or alkyl. Examples of Azo groups are provided herein.

"Cholesterol" is used in its broadest sense herein and includes cholesterol derivatives, such as oxysterols and sterols. In some embodiments, the molecule can stabilize the biomembrane.

Photoisomerization is the process of using light energy to make a structural change from a first isomer to a second isomer. In some embodiments, this involves converting a structure from a cis configuration to a trans configuration. In some embodiments, this involves converting a structure from a trans configuration to a cis configuration. In some embodiments, the photoisomerization is reversible. In some embodiments, a first wavelength of radiation will result in switching the structure from a first to a second isomer, while a second wavelength of radiation will result in switching the structure from the second isomer back to the first isomer.

"Heterocycle," as used herein denotes a cyclic compound having atoms of at least carbon and one additional different element as member of its rings. In some embodiments, the additional different element is one or more of nitrogen, carbon, or sulfur.

"Phenyl" group, as used herein, denotes a cyclic group of six carbons.

"Alkyl," as used herein, denotes any unbranched or branched, substituted or unsubstituted, saturated hydrocarbon, including $C_1$ to $C_{10}$ unbranched, saturated, unsubstituted hydrocarbons, as well as methyl, ethyl, isobutyl, and tert-butylpropyl, and pentyl.

"Substituted" has its ordinary meaning, as found in numerous patents (see, for example, U.S. Pat. Nos. 6,509,331; 6,506,787; 6,500,825; 5,922,683; 5,886,210; 5,874,443; and 6,350,759) Specifically, the definition of substituted is as broad as that provided in U.S. Pat. No. 6,509,331, which defines the term "substituted alkyl" such that it refers to an alkyl group, preferably of from 1 to 10 carbon atoms, having from 1 to 5 substituents, and preferably 1 to 3 substituents. The other above-listed patents also provide standard definitions for the term "substituted" that are well-understood by those of skill in the art.

"Sunscreen" or "sun block" includes topical products that block some amount of radiation. In some embodiments, the radiation can be from the sun. In some embodiments, the radiation can be UV radiation, such as UVA and/or UVB. In some embodiments, the radiation can be visible spectrum radiation. Sunscreens can include organic chemical compounds that absorb ultraviolet light, inorganic particulates that reflect, scatter, and absorb UV light (e.g., titanium dioxide, zinc oxide, or a combination of both), and/or organic particulates that can absorb light like organic chemical compounds, but contain multiple chromophores, may reflect and scatter a fraction of light like inorganic particulates, and can behave differently in formulations than organic chemical compounds.

An "effective amount," denotes an amount that is sufficient to achieve the noted characteristic or goal. When two or more compounds are in a composition, both of which can achieve the noted characteristic, an effective amount can be "independent," which denotes that the amount of the denoted compound is sufficient for the characteristic, even if the other compound is removed from the composition. Alternatively, the effective amount can be a "combined effective amount," denoting that the characteristic is only achieved when both compounds are present in their respective amounts.

"Sun tanner," or "tanning oil" denotes a moisturizing compound that, by keeping a surface moist, allows the surface to absorb more UV. A sun tanner that includes a composition as provided herein can allow for a sun tanner in which a desired amount of UVB is absorbed by the skin while a desired about of UVA is blocked by the molecule.

Generic Description Regenerating Embodiments

As noted above, some embodiments provided herein are directed to regenerating, radiation absorbing, molecules and sunscreen compounds that contain such molecules. Non-sunscreen uses are also contemplated and discussed herein, however, for the sake of simplicity, the use of these molecules in sun screening is provided in this generic section (with the understanding that the molecules themselves could easily be used in any of the other compositions or applications).

In some embodiments, the regenerating molecule includes an azobenzene group. In some embodiments, this group can transition from the trans to the cis conformation upon exposure to UVA energy. Furthermore, it can transition back to the trans upon exposure to visible light, among other things. An example of this transition is shown in FIG. 1. It is noted that the azobenzene compounds shown in FIG. 1 are exemplary only, and that $R^1$ and $R^2$ can be any set of molecules at any number of possible positions.

In some embodiments, the molecule includes an azobenzene group. In some embodiments, the azobenzene group is attached to a heterocycle group and/or a cholesterol group. In some embodiments, the azobenzene group has the formula of Formula I:

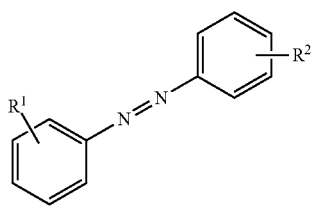

Formula I $R^1$ can include a heterocycle group or a substituted variant thereof and $R^2$ can include a cholesterol group or a substituted variant thereof.

In some embodiments, there are one or more $R^2$ groups, e.g., 1, 2, 3, 4, or 5 $R^2$ groups. In some embodiments, there are one or more $R^3$ groups, e.g., 1, 2, 3, 4, or 5 $R^3$ groups.

In some embodiments, the azobenzene group noted herein allows for reversible photoisomerization, for example, as shown in the reaction scheme of FIG. 1.

In some embodiments, the peak of the UV absorption spectra of the trans configuration is within 315 to 400 nm. In some embodiments, the majority of the absorption spectra is within 315 to 400 nm. In some embodiments, the 60, 70, 80, 90, 95, 99% or more of the absorption spectra is within 315 to 400 nm. In some embodiments, the spectra of absorption begins at 305 nm, and goes up to 400.

In some embodiments, the peak of the visible absorption spectra of the cis configuration is within about 400 to about 550 nm, e.g., 400, 410, 420, 430, 440, 450, 460, 470, 480, 490, 500, 550 nm, including any range defined between any two of the preceding values. In some embodiments, the amount of heat is an ambient level of heat. In some embodiments, the amount of heat is approximately body temperature. In some embodiments, the body is a mammal, avian, fish, or amphibian. In some embodiments, the mammal is human.

In some embodiments, the $R^2$ group can be any cholesterol or derivative thereof. In some embodiments, the $R^2$ group can be any sterol. In some embodiments, the $R^2$ group includes a molecule having the structure of Formula III:

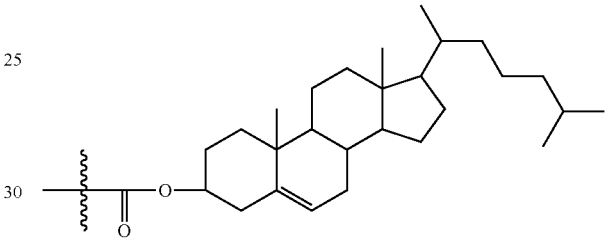

Formula III

In some embodiments, the molecule includes the structure of Formula IV:

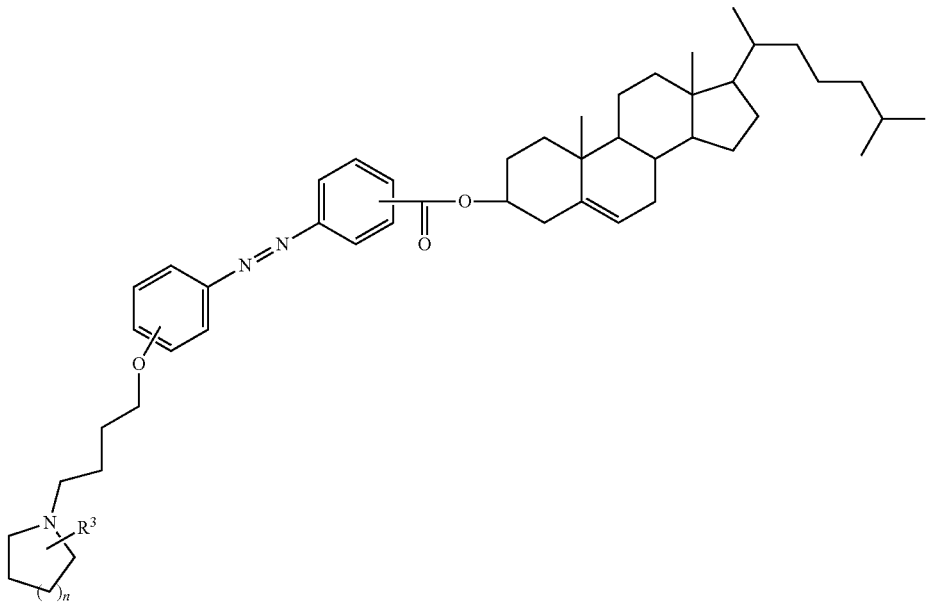

Formula IV n can be 1 or 2 and $R^3$ can be either no substitution or one or more phenyl groups.

In some embodiments, the molecule includes the structure of Formula V:

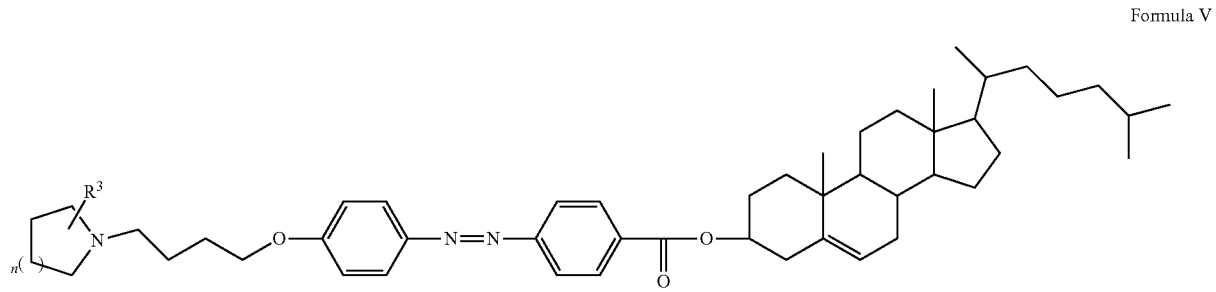

Formula V n can be 1 or 2, and $R^3$ can be either no substitution or one or more phenyl groups.

In some embodiments, when $R^3$ is a phenyl group, the phenyl is in the ortho or meso-position to the nitrogen in the heterocycle.

In some embodiments, any one or more of the molecules discussed herein can be included in a sunscreen composition. In some embodiments, the sunscreen composition includes an azobenzene. In some embodiments, the azobenzene is present in the sunscreen in an amount that is sufficient (in some embodiments independent of any other sun blocking molecules or, in some embodiments, in combination with other sun blocking molecules) to serve as a sunscreen at an SPF of at least 5, for example 5, 10, 15, 20, 25, 30, 35, 40, 45, 50, 55, 60, 65, 70, 75, 80, 85, 90, 95 or higher, including any range higher than any of the preceding values and any range defined between any two of the preceding values. In some embodiments, the azobenzene is present in the sunscreen in an amount that is sufficient (independent of any other UVB absorbing molecules) to prevent or reduce the amount of UVA passing into the surface upon which the composition is to be placed by at least 1%, for example, 2, 3, 4, 5, 6, 7, 8, 9, 10, 15, 20, 25, 30, 35, 40, 45, 50, 55, 60, 65, 70, 75, 80, 85, 86, 87, 88, 89, 90, 91, 92, 93, 94, 95, 96, 97, 98, 99, 99.1, 99.2, 99.3, 994, 99.5, 99.6, 99.7, 99.8, 99.9, 99.90, 99.95, or 99.99 percent or more, including any range above any one of the preceding values and any range defined between any two of the preceding values. In some embodiments, the azobenzene is present in the sunscreen in an amount that is sufficient (in some embodiments independent of any other sun blocking molecules or, in some embodiments, in combination with other sun blocking molecules) to serve as a sunscreen at level 4 (the highest level).

In some embodiments, the amount of the molecule in the composition is at least 3% (w/w), e.g., 3, 4, 5, 6, 7, 8, 9, 10, 15, 20, 25, 30, 35, 40, 45, 50, 55, 60, 65, 70, 75, 80, 85, 90, 95, 98, 99% or higher, including any range greater than any of the preceding values and any range defined between any two of the preceding values.

While not limiting, in some embodiments, one can employ the absorbency spectrum curve and the Lambert-Beer Law to provide guidance as to an amount of the molecule that is appropriate. In some embodiments one can obtain an apparent molar absorptivity of about 23870 $L \cdot mol^{-1} \cdot cm^{-1}$ at, for example, a maximum absorption of 358 nm. In some embodiments, one can obtain an apparent molar absorptivity of between about 15000 to 25000 $L \cdot mol^{-1} \cdot cm^{-1}$ with one or more of the molecules described herein Thus, in some embodiments, the regenerating UVA absorbing molecule is about 37% of the composition (e.g., the molecular weight is 712, and the apparent molar absorptivity is 15000 $L \cdot mol^{-1} \cdot cm^{-1}$). Of course, each of these can be changed or modified in light of a number of variables, including any of the UVA wavelengths described herein, the ability of the desired composition to block UVA, and the apparent molar absorptivity.

In some embodiments, the molecule in the sunscreen composition includes a heterocycle group attached to the azobenzene group. In some embodiments, the molecule in the sunscreen composition includes a cholesterol group attached to the azobenzene group. In some embodiments, the azobenzene group of the molecule includes the formula of Formula I:

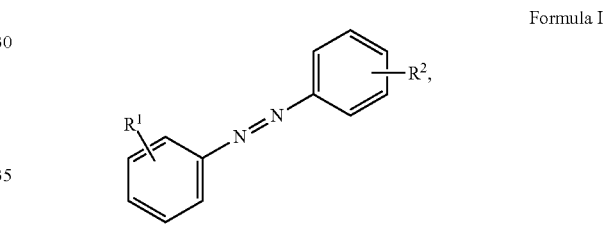

Formula I $R^1$ can include a heterocycle group or substituted variant thereof and $R^2$ can include a cholesterol group or substituted variants thereof.

In some embodiments, a pharmaceutical composition is provided that includes any one or more of the molecules described herein, combined with a pharmaceutically acceptable carrier for topical application. In some embodiments, the molecule provided herein can be used as a drug carrier.

In some embodiments, the molecule is an organic molecule. In some embodiments, the molecule is resistant to photolysis. In some embodiments, the molecule can cycle though the cis-trans conversion a number of times, e.g., 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, or more times, including any range defined between any two of the preceding values and any range above any one of the preceding values.

In some embodiments, the molecule and/or the composition does not include, or result in, a significant level of photodecomposed products following 1, 2, 3, 4, 5, 6, 7, 8, 9, 10, 11, 12, 24, 36, or 48 hours of exposure to sunlight. In some embodiments, "significant" denotes that any amount will not cause skin irritation.

Exemplary Heterocycle Embodiments

In some embodiments, the heterocycle group includes a 5, 6, or 7 membered heterocycle. In some embodiments, the heterocycle includes a 5 or 6 membered heterocycle.

In some embodiments, the heterocycle group includes nitrogen, sulfur, and/or oxygen. In some embodiments, the heterocycle includes nitrogen. In some embodiments, the heterocycle is selected from at least one of Formula VI, VII, VIII, and IX.

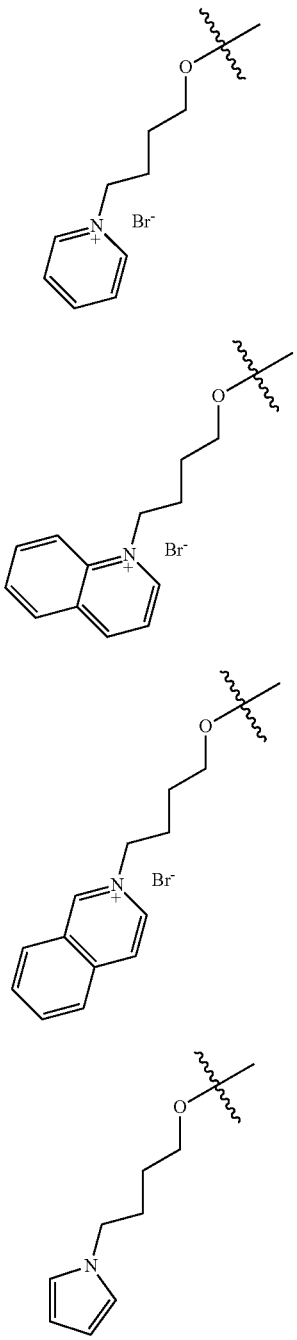

VI

VII

VIII

IX

In some embodiments, the heterocycle is connected to the structure of Formula I via an alkoxy member. In some embodiments, the heterocycle is directly connected to the structure of Formula I. In some embodiments, the heterocycle is indirectly connected to the structure of Formula I.

In some embodiments, the alkoxy member includes 1, 2, 3, 4, 5, 6, 7, or 8 carbons. The term "alkoxy" refers to any unbranched, or branched, substituted or unsubstituted, saturated or unsaturated ether, with $C_1$ $C_{10}$ unbranched, saturated, unsubstituted ethers being preferred. In some embodiments, the heterocycle group includes the structure shown in Formula II:

Formula II

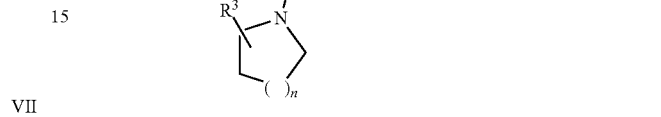

wherein n=1 or 2 and wherein $R^3$ is either no substitution or a phenyl group.

In some embodiments, $R^3$ can be in the ortho-position or meso-position to the nitrogen.

Exemplary Cholesterol Embodiments

In some embodiments, the cholesterol group can be any cholesterol group. In some embodiments, the cholesterol group includes cholesterol derivatives. In some embodiments, the cholesterol group is one that is adequately biologically safe for a topical skin composition, and/or has the function of stabilizing a biomembrane. In some embodiments, the cholesterol is selected from one or more of Formula X, XI, XII, and/or XIII.

X

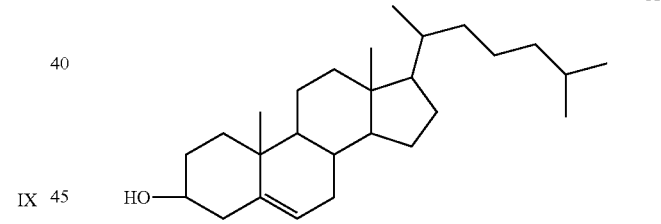

XI

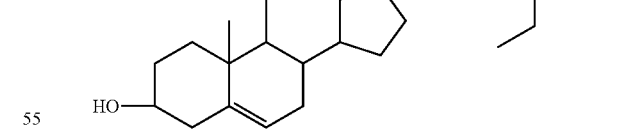

XII

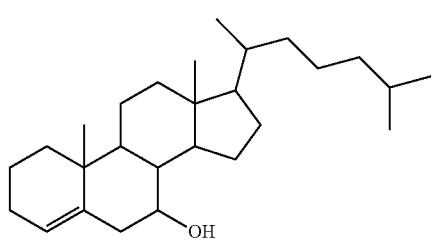

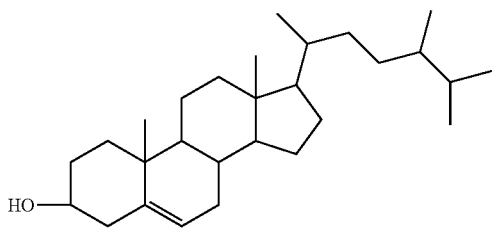

XIII

Methods of Using a Regenerating UVA Absorbing Material

In some embodiments, a method of absorbing light can be achieved by using one or more of the compounds provided herein. In some embodiments, the method includes applying a composition (that includes an azobenzene group) to a surface. The azobenzene group can be attached to at least one of the following: a heterocycle group, a cholesterol group, or both a heterocycle group and a cholesterol group. In some embodiments, one can then expose the surface to a source of ultraviolet light such that a cis form of the azobenzene is formed. In some embodiments, the trans molecule absorbs light preferentially in the UVA spectrum.

In some embodiments, one can then allow the cis form of the azobenzene to change to a trans form of the azobenzene (see, for example, FIG. 1). In some embodiments, this can include applying a temperature to the surface. In some embodiments, the temperature is any of those described herein. In some embodiments, this can include exposing the molecule and/or the surface to radiation in the visible spectrum (e.g., any of the visible radiation, for any time, at any intensity, described herein) to create the trans form of the molecule.

In some embodiments, one can then re-expose the surface to UVA radiation. As a significant amount of the molecule will be in the trans form, the molecule can once again serve as a UVA absorbing molecule (and will once again convert from trans to cis upon absorption of UVA).

In some embodiments, some molecules in a composition can transition from trans to cis while other molecules in the same composition, on the same surface can transition from cis to trans. This can occur, for example, under exposure to broad-spectrum radiation, which provides both visible and UVA radiation.

In some embodiments, the percent of molecules transitioning from trans to cis and/or cis to trans due to UVA or visible radiation is random.

In some embodiments, there can be a bias for the transition of trans to cis, such as, for example, in situations where there is more UVA radiation (e.g., from UVA lights, etc.). In some embodiments, 1, 2, 3, 4, 5, 10, 15, 20, 25, 30, 40, 50, 60, 70, 80, 85, 90, 95, 96, 97, 98, 99, 99.9% or more of the molecules are transitioning from trans to cis over a particular period, including any range defined between any to of the preceding values and any range above any one of the preceding values. In some embodiments, 1, 2, 3, 4, 5, 10, 15, 20, 25, 30, 40, 50, 60, 70, 80, 85, 90, 95, 96, 97, 98, 99, 99.9% or more of the molecules are in a given composition are in the trans state at a particular time, including any range defined between any to of the preceding values and any range above any one of the preceding values.

In some embodiments, there can be a bias for the transition of cis to trans state, such as, for example, in situations where there is more visible radiation (e.g., from typical indoor lights, etc.). In some embodiments, 1, 2, 3, 4, 5, 10, 15, 20, 25, 30, 40, 50, 60, 70, 80, 85, 90, 95, 96, 97, 98, 99, 99.9% or more of the molecules are transitioning from cis to trans state over a particular period, including any range defined between any to of the preceding values and any range above any one of the preceding values. In some embodiments, 1, 2, 3, 4, 5, 10, 15, 20, 25, 30, 40, 50, 60, 70, 80, 85, 90, 95, 96, 97, 98, 99, 99.9% or more of the molecules are in a given composition are in the cis state at a particular time, including any range defined between any to of the preceding values and any range above any one of the preceding values.

In some embodiments, the composition can be used for a method of absorbing UVA radiation. In some embodiments, the composition can be used for a method of absorbing visible radiation.

In some embodiments, a method for reducing application frequency or times of a sun block is provided. The method can involve using one or more of the molecules or compositions provided herein, allowing or using the molecule to absorb UVA (which will convert it to a cis configuration), and then transitioning the molecule back to the trans form so that the molecule will then be effective for UVA absorption again, without having to apply an additional application of sun block, thereby reducing the application frequency or times of a sun block.

In some embodiments, a method for reducing skin discomfort is provided. The method can involve using one or more of the molecules or compositions provided herein, allowing or using the molecule to absorb UVA, which will bias the molecule to a cis isomer, and then transitioning the molecule to the trans form so that the molecule will then be effective for UVA absorption again, without having to apply an additional application of sun block, thereby reducing 1) the amount of a cream or oil (which carriers the active ingredient) or the amount of active ingredient, that comes into contact with the skin, and/or 2) reducing the amount of active ingredient that breaks down on the surface of the skin. One or more of these can effectively result in reducing skin discomfort that can occur due to excessive exposure to any one or more of the above.

In some embodiments, a method of prolonged sun blocking is provided. Rather than simply lasting for 1, 2, or 3 hours, the molecule or composition provided herein can, in some embodiments, last for a longer period of time, for example 3, 4, 5, 6, 7, 8, 9, 10, 11, 12, 13, 14, 15, 16, 17, 18, 19, 20, 21, 22, 23, 24, 25 hours or more, including any range defined between any to of the preceding values and any range above any one of the preceding values.

In some embodiments, the surface includes a sun-sensitive surface. In some embodiments, the surface includes hair, skin, human skin, porcine skin, an infant's skin, etc.

In some embodiments, the surface includes non-skin options, such as glasses, art class, windows, fabric, etc.

In some embodiments, the method can employ an initial period of time in which the surface is exposed to more visible radiation than UVA radiation. This can allow for more of the molecules to be in the trans form and to serve for absorption of UVA once UVA exposure begins. In some embodiments, the molecule and/or composition is applied at least 30 minutes before the surface is exposed to direct UV light, e.g., 25, 20, 15, 10, 9, 8, 7, 6, 5, 4, 3, 2, 1 minute or less before the surface is exposed to a source of UVA from which some amount of UVA protection is desired, including any range defined between any two of the preceding values and any range below any of the preceding values.

The UVA source can be any of a number of sources, and can include, for example, natural, such as the sun and artificial sources, such as UVA lamps, black lights, ultraviolet LEDs, bug zapper lights, ultraviolet lasers, etc.

In some embodiments, a kit is provided that includes a UVA radiation source and a molecule or composition provided herein. In some embodiments, a kit is provided that includes a UVA blocking device, such as UVA blocking sunglasses or other protective eyewear, and a molecule or composition provided herein.

In some embodiments, the molecule and/or composition can be applied as or in a topical formulation.

In some embodiments, the allowing and/or promoting the transition from the cis form of the azobenzene group to the trans form of the azobenzene group occurs at a temperature between 26 and 43 degrees Celsius, e.g., 27, 28, 29, 30, 31, 32, 33, 34, 35, 36, 37, 38, 39, 40, 41, 42, or 43 degrees, including any range above or below any of the preceding values and any range defined between any two of the preceding values. In some embodiments, the method occurs at about body temperature. In some embodiments, the cis to trans transition occurs at any of the above temperature ranges. In some embodiments, the trans to cis transition can occur at any of the above temperature ranges. In some embodiments, both transitions occur at any of the above temperature ranges.

In some embodiments, the transition of the cis form of the azobenzene to the trans form of the azobenzene occurs via the presence of radiation having a wavelength of greater than about 380 nm. In some embodiments, the molecule has an absorption spectra as shown in, for example FIGS. 3A-4C or FIGS. 5A-5C.

In some embodiments, a method of reactivating (or "regenerating") a sunscreen is provided. In some embodiments, the method can include providing a sunscreen that can include a trans azobenzene. The method can further include exposing the trans azobenzene to ultraviolet light for a first period of time to convert the trans azobenzene to a cis azobenzene. The transition from the trans to the cis occurs via the absorption of UVA by the molecule. In some embodiments, one can allow (and/or promote) the cis azobenzene to return to the trans azobenzene to form reactivated trans azobenzene to place the molecule back into a state where it can preferentially absorb UVA.

In some embodiments, any of the methods can further include exposing the reactivated trans azobenzene to ultraviolet light for one or more additional rounds of exposure to UVA, e.g., 1, 2, 3, 4 5, 6, 7, 8, 9, 10, 15, 20, 25, 30, 35, 40, 50, 60, 70, 80, 90, or 100 times, including any range above any of the preceding values and any range defined between any two of the preceding values.

In some embodiments, a method for providing UVA protection is provided. The method can include applying a regenerating UV absorbing molecule to the surface of a subject's skin, wherein enough of the UV absorbing molecule is in a UVA absorbing configuration so as to meaningfully serve to reduce the amount of UVA contacting the subject's skin. In some embodiments, "meaningfully serve" denotes that the subject receives a health benefit from the presence of the UV absorbing molecule, such as less collagen destruction or degradation. In some embodiments, there is a sufficient amount so as to reduce collagen destruction or degradation by at least 5, 10, 15, 20, 25, 30, 40, 50, 60, 70, 80, 85, 90, 95, 96, 97, 98, 99, 99.9, 99.99, percent or more, including any range above any of the preceding values and any range defined between any two of the preceding values.

In some embodiments, under irradiation with a wavelength of 300 nm to 400 nm, azobenzol can change from trans to cis, while absorbing (and thus protecting from) UVA radiation. In some embodiments, once in the cis configuration, it will not absorb the lower wavelengths of UVA as strongly, the cis configuration can absorb visible light, with light stability which is inferior to that of trans configuration, and will change from cis to trans when being heated or under irradiation of light >380 nm.

Method of Making Regenerating UV Absorbing Molecules

In some embodiments, a method of making a regenerating UV absorbing molecule is provided. In some embodiments, this includes providing an azo compound and attaching a cholesterol group to the azo compound.

While the cholesterol group can be attached by any manner known in the art, in some embodiments, the cholesterol group is attached to the azo compound by an esterification reaction. In some embodiments, the azo compound is provided by a diazo reaction.

In some embodiments, the maximum absorbing optical wavelength can be changed by substitution of the groups on the benzene ring. In some embodiments, addition of a fatty group, as opposed to an aromatic group, results in a higher molar absorption coefficient. Additional alterations and examples of the molar absorption are shown in the Examples below.

Figure 2:
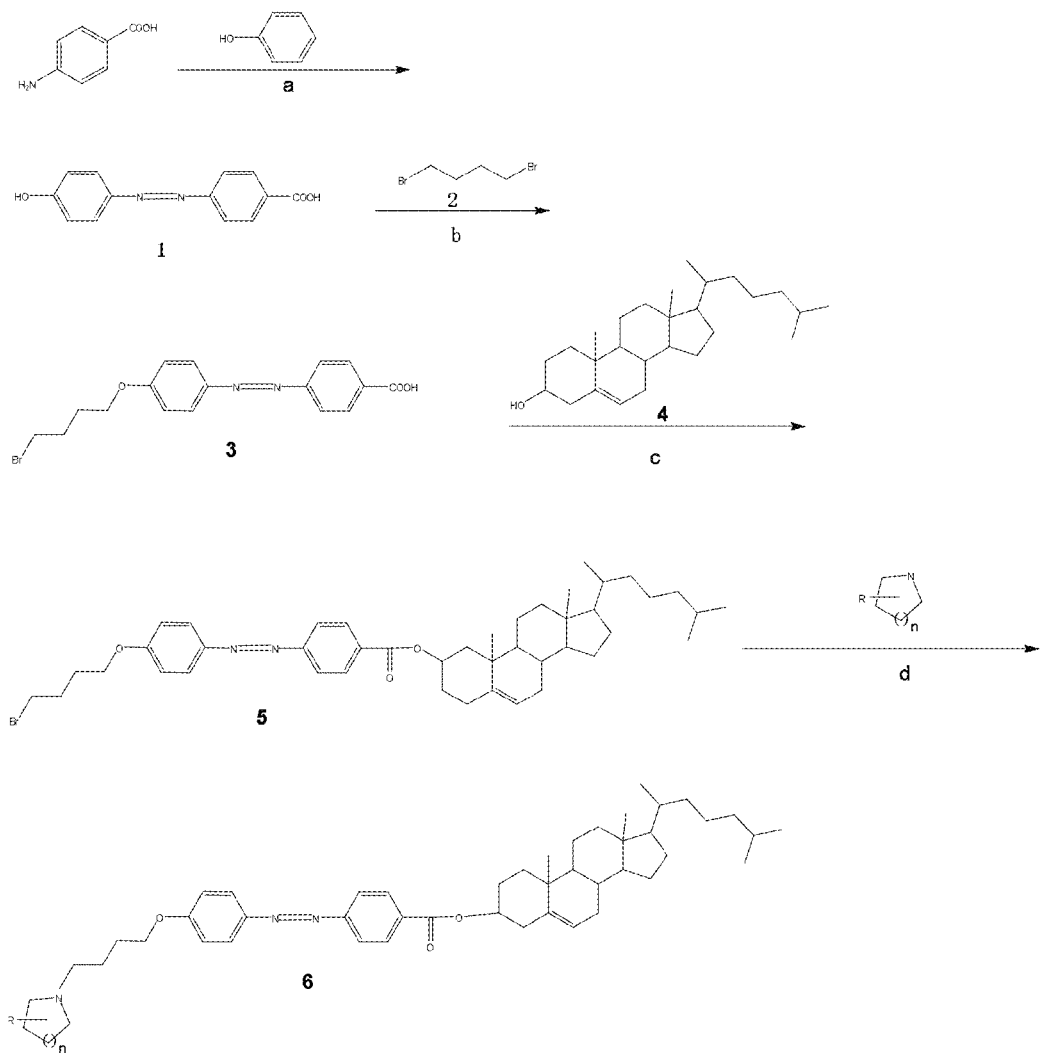
FIG. 2 is a depiction of a synthesis pathway for some embodiments provided herein.

FIG. 2 depicts one reaction scheme for producing an exemplary molecule as provided herein. As shown in reaction, p-aminobenzoic acid (50 mmol) can be combined with hydrochloric acid to produce the diazonium salt, which can be combined with phenol and NaOH (100 mmol) to obtain a starting azo compound (e.g., 1, FIG. 2). This can be combined with 1,4-dibromobutane (e.g., 2, FIG. 2) to obtain 4-[4-(4-bromo-butoxy)-phenylazo]-benzoic acid (e.g., 3, FIG. 2). 3 can then be combined with a desired cholesterol (e.g., 4, FIG. 2) to obtain 4-(4-bromobutoxyl)-4'-((cholesteryloxy)carbonyl)azobenzene (e.g., 5, FIG. 2). This can be combined with a molecule appropriate for the desired heterocycle group, such as pyridine, quinoline, and/or isoquinoline to produce a desired product (e.g., 6, FIG. 2). Additional specific options and conditions for the synthesis of exemplary embodiments are provided in Examples 1-6 below. In some embodiments, one or more of the reactions noted above can take place in a different order.

Additional Sun Screen Ingredients

In some embodiments, the UVA absorbing molecule provided herein can be used or employed in a sunscreen composition. In some embodiments, the composition can include additional ingredients that are appropriate for a sunscreen, including, for example, one or more ingredient of the following: p-Aminobenzoic acid, Padimate O, Phenylbenzimidazole sulfonic acid, Cinoxate, Dioxybenzone, Oxybenzone, Homosalate, Menthyl anthranilate, Octocrylene, Octyl methoxycinnamate, Octyl salicylate, Sulisobenzone, Trolamine salicylate, Avobenzone, Ecamsule, Titanium dioxide, Zinc oxide, Cinnamates (octyl methoxycinnamate (OMC), Ethylhexyl p-Methoxycinnamate, Ensulizole, Octinoxate, Octyl dimethyl paba, and any combination thereof. In some embodiments, the composition can include one or more ingredient selected from the following: Avobenzone, Parsol 1789, Dioxybenzone (UVB, UVAII), Ecamsule, Menthyl Anthranilate, Meradimate, Oxybenzone (benzophenone, benzophenone-3), Sulisobenzone (UVB, UVAII), and any combination thereof.

In some embodiments, the composition does not include a photostabilizer.

In some embodiments, the sunscreen composition is a sun block. In some embodiments, the sunscreen composition is, or is part of, a sun tanner. In some embodiments, the sunscreen composition blocks most if not all of UVA and UVB. In some embodiments, while allowing some UVB to pass (e.g., at a level that is adequate for vitamin D production, the composition includes enough UVA blocker to still block a substantial amount of UVA, e.g., 10, 20, 30, 40, 50, 60, 70, 80, 90, 95, 96, 97, 98, 99, 99.9, 99.99 percent or more of the UVA, including any range above any of the preceding values and any range between any two of the preceding values.

In some embodiments, the sunscreen composition also includes at least one ingredient, such as water. In some embodiments, the sunscreen composition is formulated as an oil, cream, lotion, spray, lipstick, ointment, wax, or gel, and thus, can include ingredients for such a composition.

In some embodiments, the sunscreen composition is formulated for sensitive skin, and thus, includes no or minimal ingredients that can cause skin irritation for infants, children, or adults. In some embodiments, the composition is formulated for humans. In some embodiments, the composition is formulated for mammals, birds, fish, or amphibians.

In some embodiments, the composition is formulated and/or appropriate for use directly on the skin. In some embodiments, the composition is not formulated and/or appropriate for use directly on the skin. In some embodiments, the composition is formulated for use on materials which are frequently touched by humans or other mammals. In some embodiments, the composition is formulated for use on surfaces that are not frequently touched by humans (such as the surfaces of protective art glass).

In some embodiments, additional compounds for making the molecules water-safe on the surface (e.g., a "water-resistant" sunscreen) can be added to the composition.

In some embodiments, a sunscreen composition is provided. The composition can include an azobenzene that is to at least one of the following: a heterocycle group, a cholesterol group, or both a heterocycle group and a cholesterol group. In some embodiments, the composition includes an effective amount of the regenerating UV absorbing molecules so as to provide a desired level of protection against UV. In some embodiments, it is a desired amount of protection for a subject's skin. In some embodiments, it is protection against UVA wavelengths. In some embodiments, it is sufficient for 0.5, 1, 2, 3, 4, 5, 6, 7, 8, 9, 10, 11, 12, 13, 14, 15, 16, 17, 18, 19, 20, 21, 22, 23, 24 or more hours against a source of UVA for effective protection of skin.

In some embodiments, the sunscreen includes a trans form of an azobenzene molecule. In some embodiments, the sunscreen includes a cis form of an azobenzene molecule. In some embodiments, the sunscreen includes a trans and a cis form of an azobenzene molecule.

Additional Uses for UV Absorbing Molecules

In some embodiments, the molecule can be applied in intelligent drug delivery systems.

Additional Embodiments and Optional Advantages

In some embodiments, the molecules and/or compositions provided herein have low skin irritation and lower sensitization. In some embodiments, the decomposition products of the molecules and/or compositions provided herein have low skin irritation and lower sensitization. In some embodiments, the photo-decomposition products of the molecules and/or compositions provided herein have low skin irritation and lower sensitization.

In some embodiments, one or more of: low absorption efficiency, inferior radiation stability, and strong skin irritation can be addressed by one or more of the molecules and/or compositions provided herein.

In some embodiments, one or more of the molecules and/or compositions provided herein have higher radiation absorptivity in the UVA region.

In some embodiments, under body temperature and in visible radiation, the compound can revert to a trans conformation, to again have the ability of absorbing UVA. In some embodiments, the compound can be used repeatedly, and once applied, can, at least in the trans form, maintain its effectiveness. In some embodiments, the compound has one or more of the following merits: (1) it can be exposed to UVA (long wavelength UV) repeatedly without photodecomposition; (2) under visible radiation, the compound can revert to a state in which it can once again function to absorb UVA to ensure smaller dosage and fewer application times; and/or (3) it can meet the safety requirements of cosmetics.

In some embodiments, the compounds are not, or are not meaningfully photolytic (e.g., do not break down beyond use under normal use).

EXAMPLE 1

The present Example outlines a process in the preparation of the some of the molecules provided herein. Ice cooled aqueous $Na_2NO_2$ (60 mmol, 30 mL) was cautiously poured into a stirred solution of p-aminobenzoic acid (50 mmol) in hydrochloric acid (14 mL concentrated HCl in 60 mL $H_2O$) by keeping the temperature below 5° C. After 20 min, this mixture that contains the diazonium salt was poured into an ice-cooled aqueous solution of phenol (50 mmol) and NaOH (100 mmol). The reaction mixture was stirred at about 5° C. for 1 hour, then neutralized. The resulting yellow precipitates were collected, washed with water and methanol, crystallized from hot NaHCO3 solution. Pure 1 (FIG. 2) was obtained, yield 75%. The product had the following characteristics: IR (KBr) $\upsilon/cm^{-1}$: 3115, 1665, 1590, 1500, 1468, 1428.

EXAMPLE 2

The present Example outlines a process in the preparation of the some of the molecules provided herein. 4(4-hydroxyphenyl)azo)benzoic acid 1 (FIG. 2) (20 mmol), potassium carbonate (40 mmol), 1,4-dibromobutane 2 (80 mol) and a trace of potassium iodide were refluxed for 48 h in 200 mL dry acetone. After cooling, the precipitate was collected, dried and hydrolyzed with 10% alcoholic KOH, then acidified with HCl, filtered and crystallized from hot hexane/alcohol. Pure 3 was obtained, yield 80%. The product had the following characteristics: IR (KBr) $\upsilon/cm^{-1}$: 1681, 1602, 1581, 1501, 1427, 1277, 1248, 1142.

EXAMPLE 3

The present Example outlines a process in the preparation of the some of the molecules provided herein. 4-[4-(4-bromobutoxy)-phenylazo]-benzoic acid 3 (FIG. 2) (15 mmol) and cholesterol 4 (15 mmol) were dissolved in 80 mL of dichloromethane under a nitrogen atmosphere. The solution was maintained at 0° C. by ice bath. The dicyclohexylcarbodiimide (DCC) (16 mmol) and a trace of (dimethylamino)-pyridine (DMAP) were then added. The reaction mixture was stirred for 8 h at room temperature. The reaction mixture was filtered and the residue obtained following removal of the solvent under reduced pressure was chromatographed on a silica gel column with hexane/chloroform (2:1) as solvent systems. Pure 5 was obtained, yield 55%. The product had the following characteristics: IR (KBr) $\upsilon/cm^{-1}$: 2930, 2860, 1722, 1708, 1602, 1500, 1468, 1282, 1257, 1143, 1116.

EXAMPLE 4

The present Example outlines a process in the preparation of the some of the molecules provided herein. 4-(4-bromobutoxyl)-4'-((cholesteryloxy)carbonyl)azobenzene 5 (FIG. 2)

(3 mmol) and pyridine (6 ml) were added to THF (100 ml) and then refluxed for 3 days. After the reaction mixture was cooled to room temperature and filtered. The solvent was removed. The crude product was further purified by passing through a silica gel column using chloroform-methyl alcohol as solvent and recrystallization to afford pure 6a, yield 60%. The product had the following characteristics: $^1$H NMR (400 MHz, CDCl3, ppm): 9.59 (2H, d, J=8 Hz), 8.45 (1H, t, J=8 Hz), 8.1 (2H, d, J=8.8 Hz), 8.09 (2H, t, J=8 Hz), 7.91-7.98 (4H, m), 7.00 (2H, d, J=8 Hz), 5.43 (1H, s), 5.21 (1H, d, J=8 Hz), 4.18 (2H, t, J=5.2 Hz), 0.68-2.50 (49H, m). MS (ESI): 744 (M$^+$−79). IR (KBr) υ/cm$^{-1}$: 3383, 2930, 2860, 1713, 1637, 1597, 1496, 1461, 1263, 1101, 1027, 802, 688.

EXAMPLE 5

The present Example outlines a process in the preparation of the some of the molecules provided herein. 4-(4-bromobutoxyl)-4'-((cholesteryloxy)carbonyl)azobenzene 4 (FIG. 2) (3 mmol) and quinoline (9 ml) were added to THF (100 ml) and then refluxed for 3 days. After the reaction mixture was cooled to room temperature and filtered. The solvent was removed. The crude product was further purified by passing through a silica gel column using chloroform-methyl alcohol as solvent and recrystallization to afford pure 6b, yield 55%. The product had the following characteristics: $^1$H NMR (400 MHz, CDCl$_3$, ppm): 9.01 (1H, d, J=8 Hz), 8.97 (1H, s), 8.80 (1H, d, J=8 Hz), 8.56 (1H, d, J=8 Hz), 8.25 (1H, d, J=8 Hz), 8.18 (2H, d, J=4 Hz), 8.09 (2H, t, J=8 Hz), 7.91-7.00 (2H, d, J=8 Hz), 5.43 (1H, s), 4.90 (1H, d, J=8 Hz), 4.18 (2H, t, J=5.2 Hz), 0.68-2.50 (49H, m). MS (ESI): 794 (M$^+$−79). IR (KBr) υ/cm$^{-1}$: 2930, 1712, 1600, 1467, 1461, 1274, 1139, 1114, 842, 696.

EXAMPLE 6

The present Example outlines a process in the preparation of the some of the molecules provided herein. 4-(4-bromobutoxyl)-4'-((cholesteryloxy)carbonyl)azobenzene 4 (FIG. 2) (3 mmol) and isoquinoline (9 ml) were added to THF (100 ml) and then refluxed for 3 days. After the reaction mixture was cooled to room temperature and filtered. The solvent was removed. The crude product was further purified by passing through a silica gel column using chloroform-methyl alcohol as solvent and recrystallization to afford pure 6c, yield 60%. The product had the following characteristics: $^1$H NMR (400 MHz, CDCl$_3$, ppm): 9.01 (1H, d, J=8 Hz), 8.97 (1H, s), 8.80 (1H, d, J=8 Hz), 8.56 (1H, d, J=8 Hz), 8.25 (1H, d, J=8 Hz), 8.18 (2H, d, J=4 Hz), 8.09 (2H, t, J=8 Hz), 7.91-7.00 (2H, d, J=8 Hz), 5.43 (1H, s), 4.90 (1H, d, J=8 Hz), 4.18 (2H, t, J=5.2 Hz), 0.68-2.50 (49H, m). MS (ESI): 794 (M$^+$−79). IR (KBr) υ/cm$^{-1}$: 2930, 1712, 1600, 1467, 1461, 1274, 1139, 1114, 842, 696.

EXAMPLE 7

The present example outlines a use of the regenerating UVA absorbing molecule as a sun blocking agent.

A subject at risk of being exposed to UVA applies the regenerating UVA absorbing molecule of Formula V to the subject's skin.

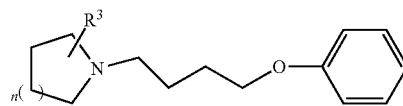

Formula V n = 1, and R$^3$ is no substitution.

The amount applied is sufficient to provide the desired protection to the subject, by the presence of the regenerating UVA absorbing molecule alone, although other sun blocking agents can optionally be present. Enough of the regenerating UVA absorbing molecule is present in the trans form so that the molecules reduce the UVA absorbed by the skin by at least 50 percent.

EXAMPLE 8

The present example outlines a method of regenerating the regenerating UVA absorbing molecule.

After being exposed to the UVA source (such as the sun) for two to three hours, the subject from Example 7 can allow the regenerating UVA absorbing molecules to regenerate more completely. The subject can prevent or reduce the amount of sunlight (and thus UVA) contacting their skin (and can optionally go inside) for ten minutes to allow at least some of the cis confirmation of the regenerating UVA absorbing molecules to isomerizes back to the trans form, thereby regenerating the regenerating UVA absorbing molecules.

EXAMPLE 9

The present example outlines a method of regenerating the regenerating UVA absorbing molecule.

While the subject from Example 7 is being exposed to the UVA source (the sun) for two to three hours, the subject's skin is also exposed to visible light from the sun at a sufficient level to change at least some of the cis isomers back to the trans isomers for the regenerating UVA absorbing molecules, thereby regenerating the regenerating UVA absorbing molecules.

EXAMPLE 10

The present example outlines a method of reusing the regenerated regenerating UVA absorbing molecules from Example 8.

The subject from Example 8 can then reexpose their treated skin to sunlight or a UVA source. The regenerated regenerating UVA absorbing molecule will once again absorb UVA radiation and reduce the amount of UVA making it into the subject's skin.

EXAMPLE 11

This example provides an example of a sunscreen composition. The molecule of Formula V:

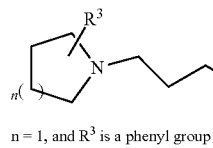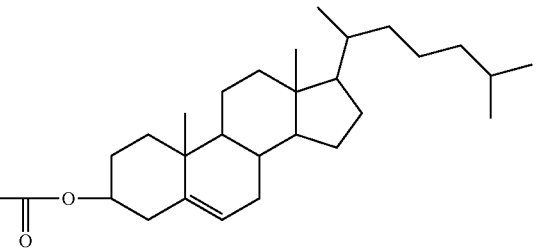

Formula V n = 1, and R³ is a phenyl group is mixed with an oil carrier. The amount of the molecule of Formula V in the oil carrier is sufficient to block at least 50 percent of the UVA present in sunlight at sea level when the oil is applied and rubbed into a subject's skin (when at least 90% of the molecule is in the trans form). The amount of the molecule present in the composition will be between 11 percent and 37 percent (w/w).

EXAMPLE 12

This example provides an example of a sunscreen composition. The molecule of Formula V:

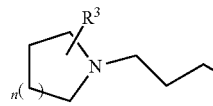

Formula V n = 2, and R³ is no substitution is combined with a carrier to form a mixture. The mixture is placed within a can that is configured to apply the mixture in an aerosolized manner. The amount of the molecule of Formula V in the mixture is sufficient to block at least 95 percent of the UVA present in sunlight at sea level when the mixture is applied (when at least 90% of the molecule is in the trans form). The amount of the molecule present in the composition will be between 25 percent and 37 percent (w/w). The mixture can also include a UVB blocking molecule.

EXAMPLE 13

This example provides a method for verifying how much of a regenerating UVA absorbing molecule (or a composition including such a molecule) can be included for a desired UVA blocking result. The UVA absorbing properties of a molecule from Example 6 or a composition of Examples 11 and 12 can be verified as follows. A known amount of the molecule or compound is placed on a UVA radiation transparent surface. The surface is placed over a UVA detector (which can include a UVA filter, which only allows UVA to pass, in line with a photomultiplier tube or CCD). The surface is then exposed to UVA, and the amount of UVA that passes through the coated surface, to the detector is determined. The amount of the molecule or composition can be adjusted until the desired amount of UVA absorption is achieved. The amount of the molecule in the cis or trans configuration can also be adjusted via the use of visible light to force more of the molecule into the trans configuration. Thus, the amount of molecule used to block or absorb various intensities of UVA can be determined.

The amount of molecule used to block a given intensity of UVA can then be used to determine a particular amount of molecule to be employed in a particular sun block composition. Not only can the above result be taken into account, but one can also factor in how much UVA exposure is acceptable to the skin (or other surface), and how much UVA is expected to come from a given UVA source (such as the sun). Thereby determining how much of a molecule should be present in any given composition.

EXAMPLE 14

This Example outlines one set of experiments conducted to demonstrate the light absorbing ability of some embodiments of the regenerating UVA absorbing molecules.

Photoisomerization tests were carried out on compounds PyB (Formula XIV) and iQB (Formula XV), which were synthesized and characterized by MS, IR, $^1$H NMR spectra.

using an UV-Vis spectrophotometer (U3010, Hitachi, Japan). All experiments were carried out at room temperature unless otherwise stated.

Figure 3A:
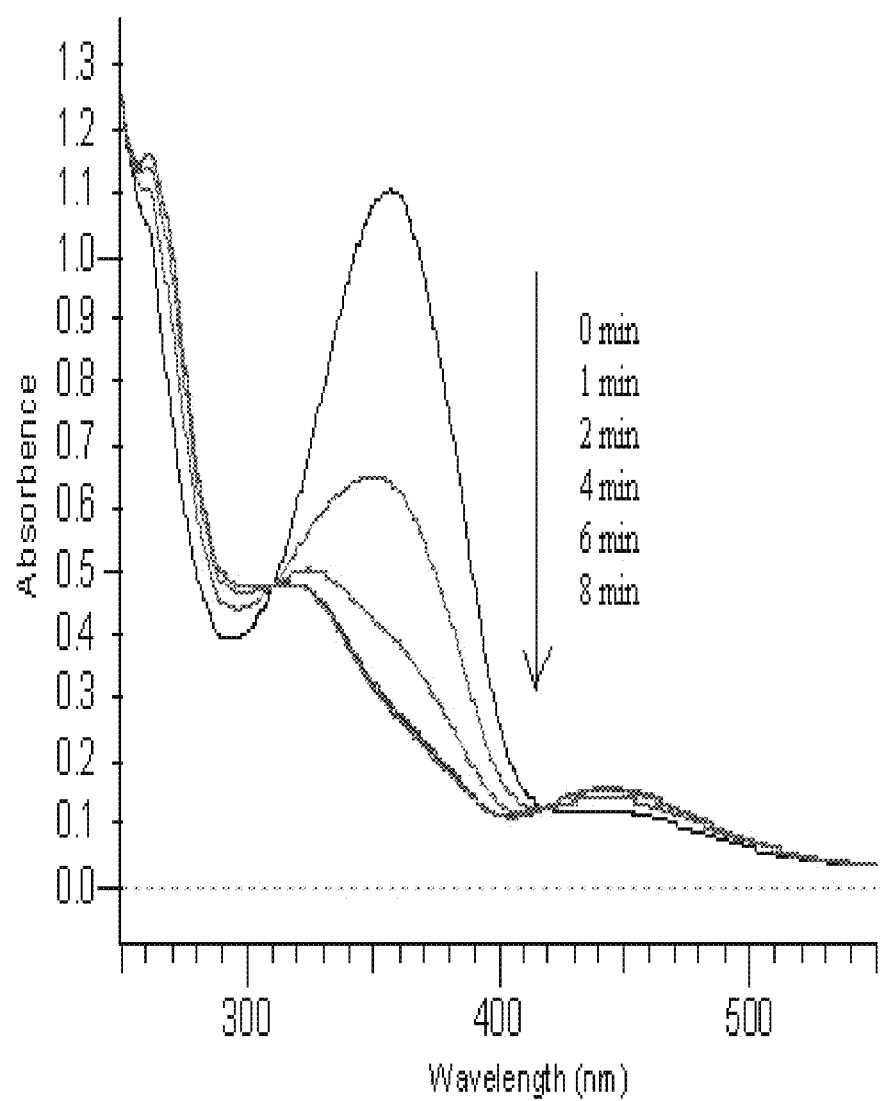
FIGS. 3A-3C are graphs depicting UV-Visible spectral change following UV light irradiation of PyB (3A), visible light irradiation (3B), and natural light irradiation (3C) for different times.
Figure 3B:
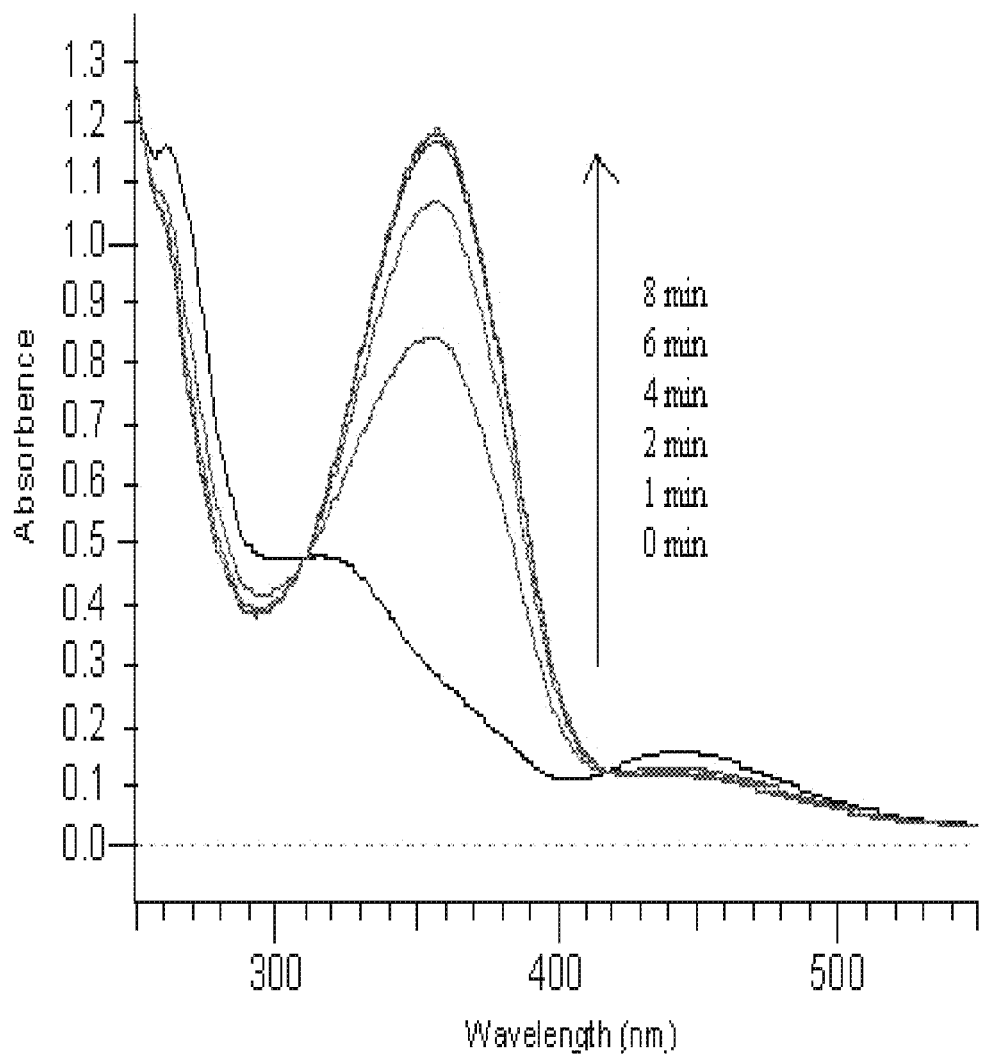
Figure 3C:
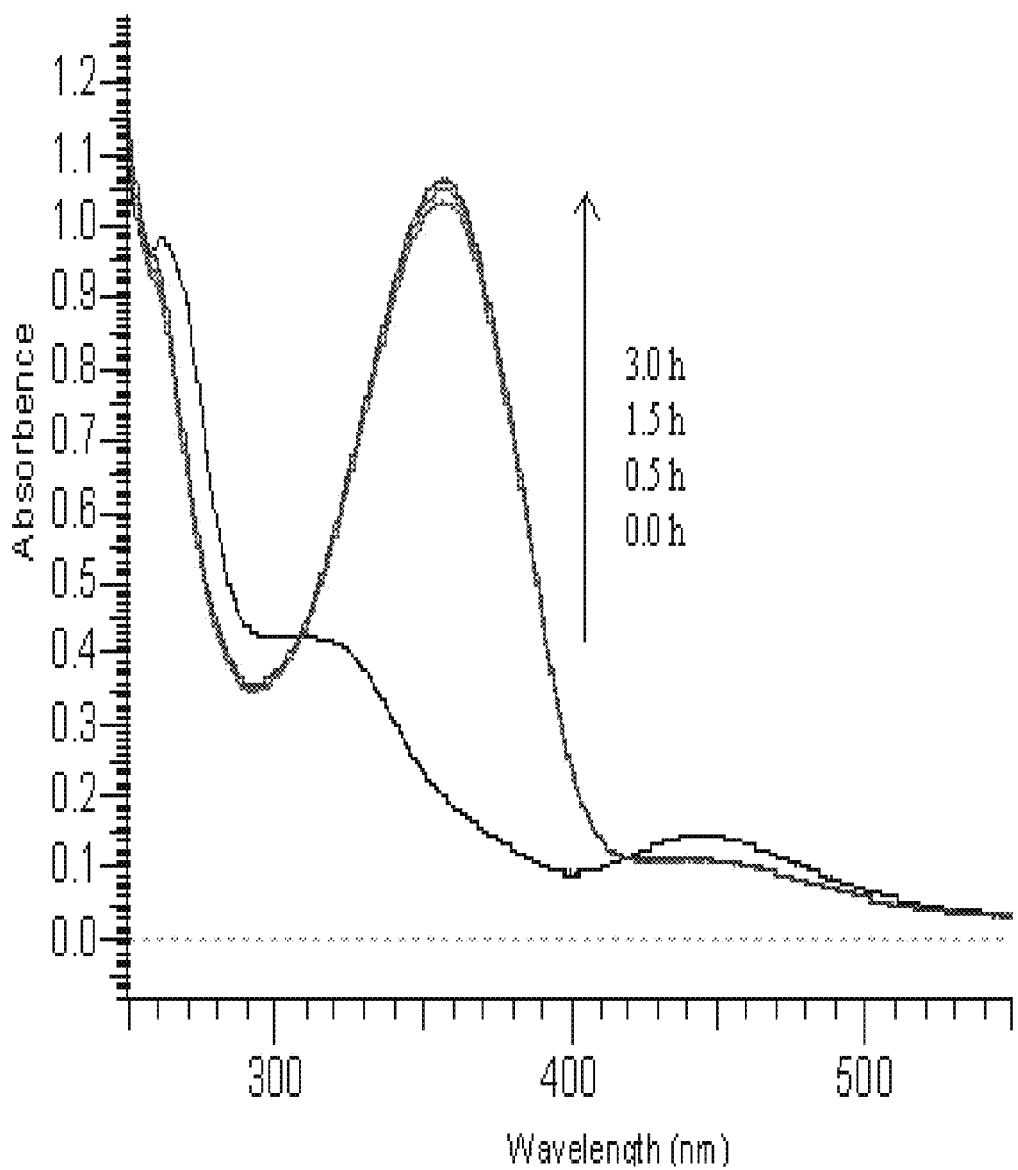
Figure 4A:
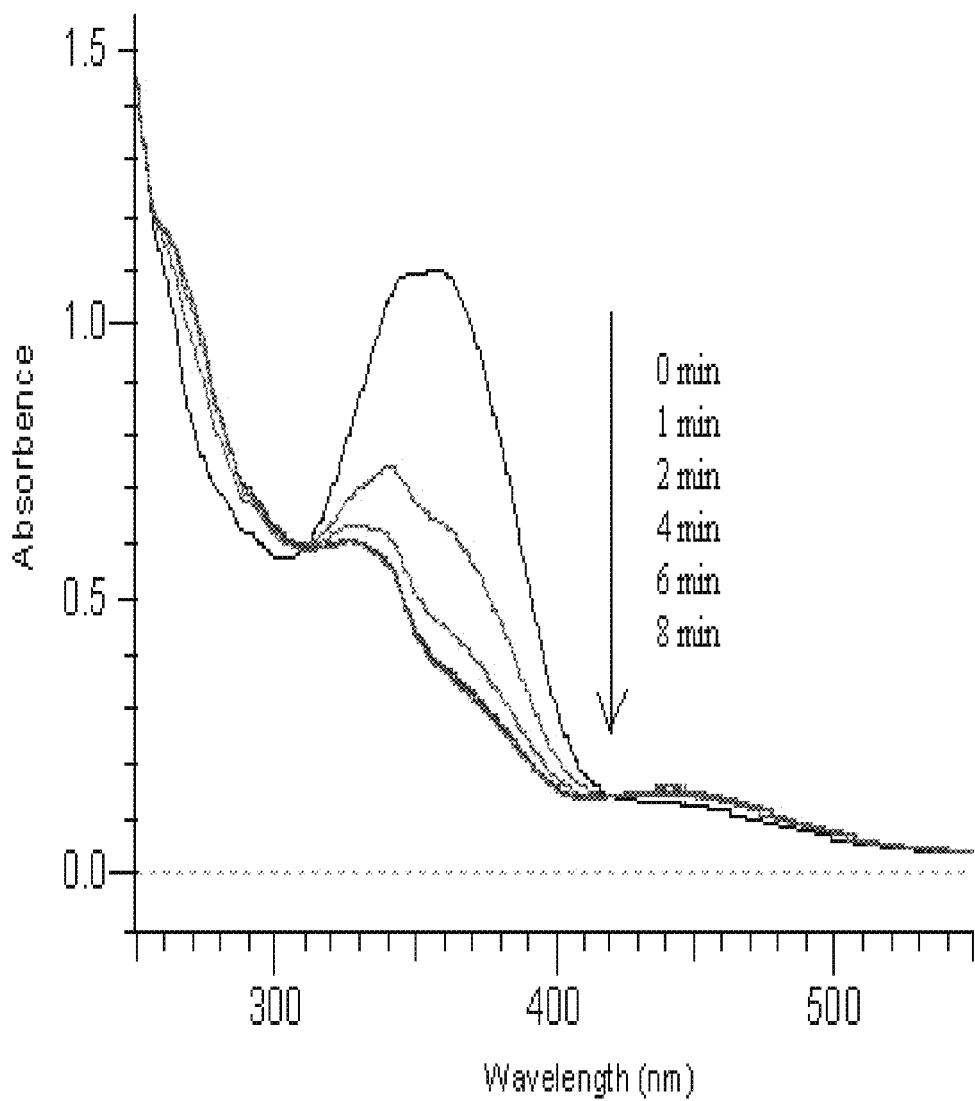
FIGS. 4A-C are graphs depicting UV-Visible spectral change following UV light irradiation of iQB (4A), visible light irradiation (4B), and natural light irradiation (4C) for different times.
Figure 4B:
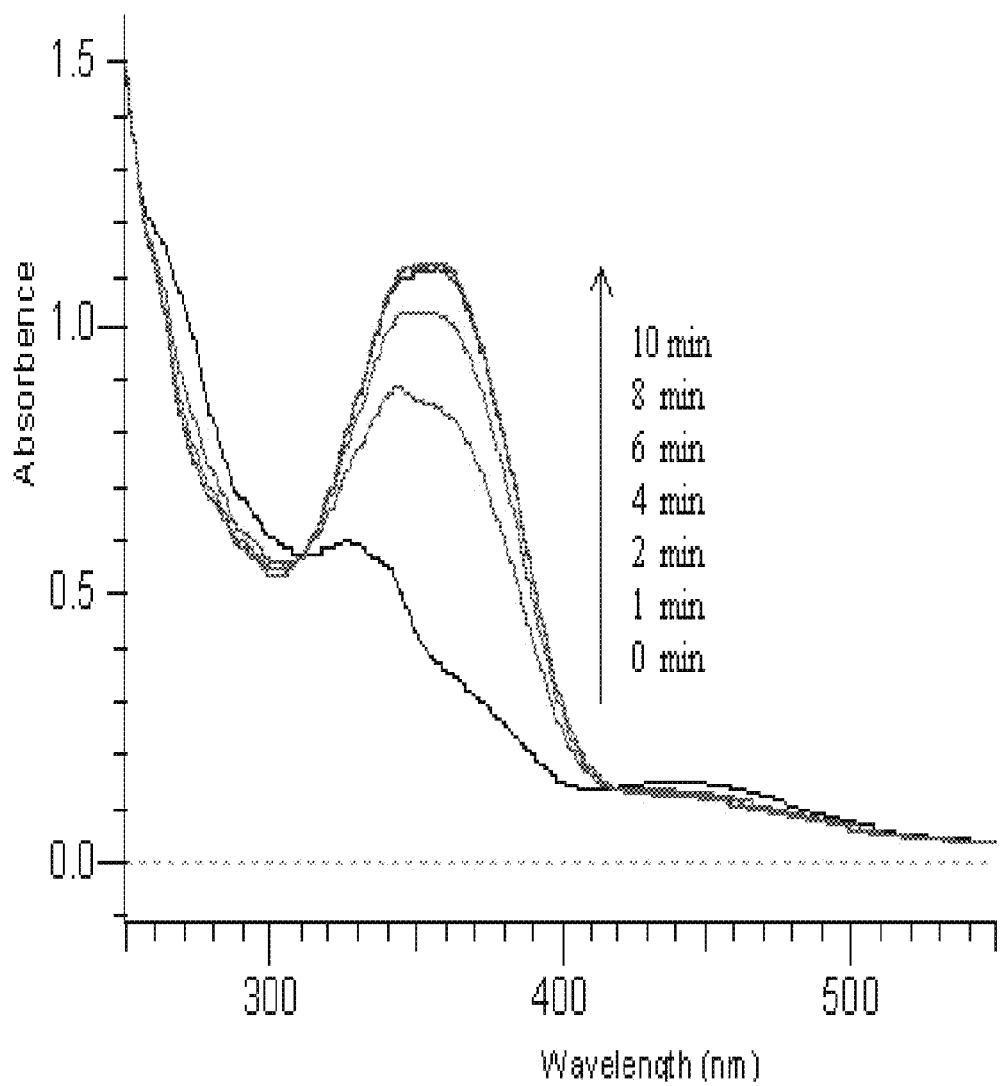
Figure 4C:
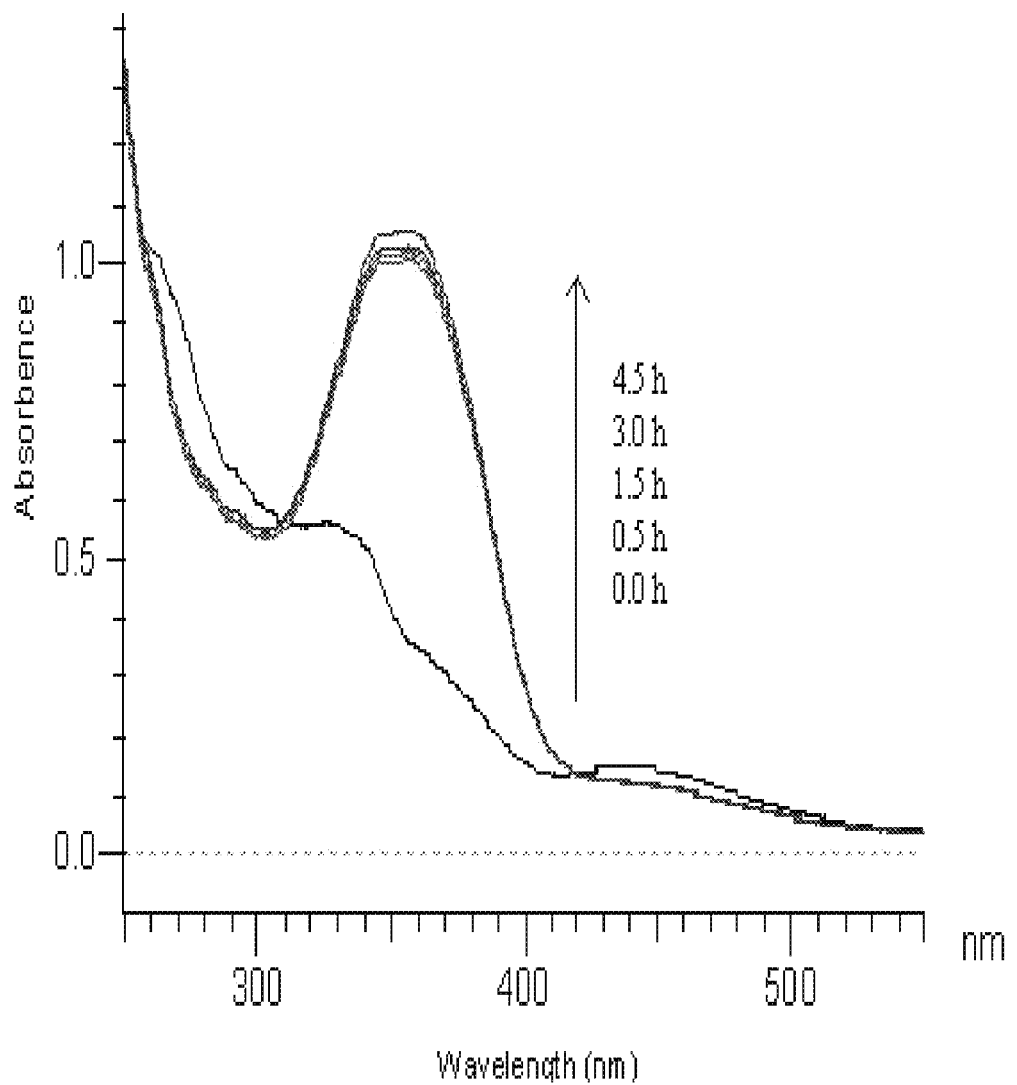

It was estimated from the spectral change that trans-PyB and iQB were converted into the cis-PyB or iQB after 6 or 8 min (respectively) of UV light irradiation (FIGS. 3A and 4A); it took 8 min of visible light irradiation to reach the photostationary state of trans-PyB or iQB (FIGS. 3B and 4B) and 3.0 h of natural light irradiation to reach the photostationary state of trans-PyB or iQB (FIGS. 3C and 4C).

The molar absorptivity in $CHCl_3$ was then determined, the results of which are shown in Table 14.1 below:

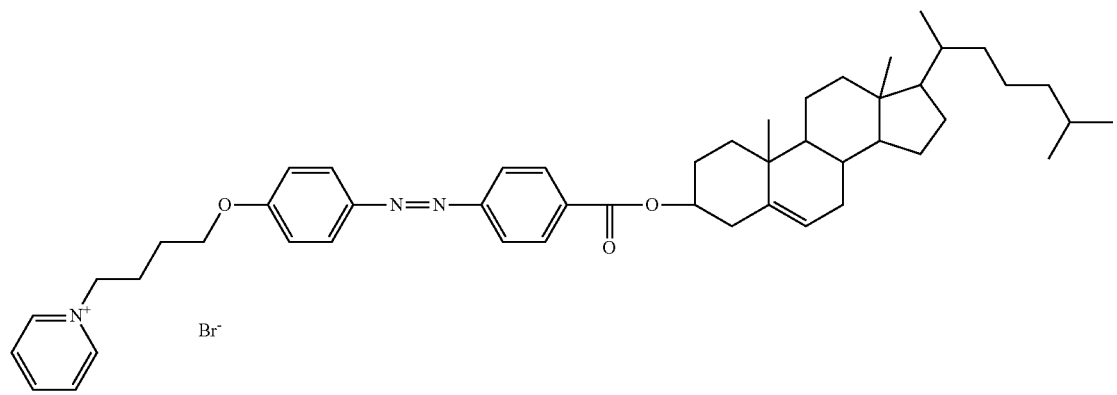

Fromula XIV

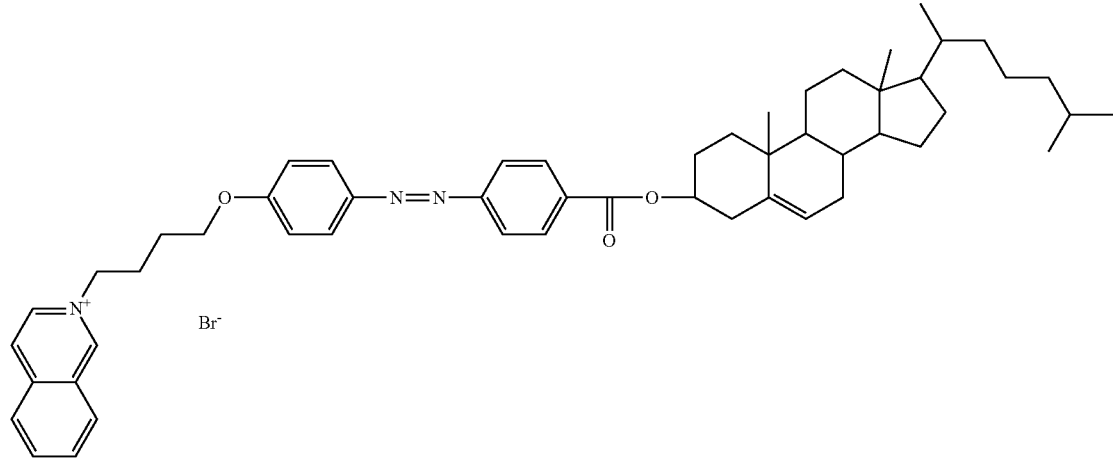

Formula XV

The tests included observing the UVA-absorbing condition before and after light exposure and noting the molar absorption coefficient. The test also included determining the photo isomerization conditions under illumination of UVA, visible light and daylight. The compounds were irradiated with a 400 W high-pressure Hg lamp (LCE-9, Zhengzhou, China). A bandpass filter ($\lambda_T$=275~400 nm) was used for UV light and a bandpass filter ($\lambda_T$>400 nm) was used for visible light. The light distance was 20 cm. For natural light irradiation, samples were irradiated with fluorescent lamps (21 W×2, luminous intensity about 500 lx), and the light distance was 120 cm. The ultraviolet spectra of $CHCl_3$ were measured

TABLE 14.1

| Subtracts | $\lambda_{CHCl_3}$\nm | A | $C^a$\mg/mL | $\kappa$(L/mol·cm) |
|---|---|---|---|---|
| avobenzone | 320 | 0.334 | 0.01 | 10354 |
| | 358 ($\lambda_{max}$) | 0.770 | | 23870 |
| | 360 | 0.765 | | 23715 |
| | 400 | 0.074 | | 2294 |
| CDBA | 357 ($\lambda_{max}$) | 0.335 | 0.01 | 24726 |
| (XVI) | 442 | 0.043 | 0.01 | 3174 |
| PyB (XIV) | 356 ($\lambda_{max}$) | 0.526 | 0.03 | 14464 |
| | 442 | 0.081 | 0.03 | 2227 |

TABLE 14.1-continued

| Subtracts | $\lambda_{CHCl3}$\nm | A | $C^a$\mg/mL | κ(L/mol·cm) |
|---|---|---|---|---|
| iQB (XV) | 357 ($\lambda_{max}$) 442 | 0.242 | 0.01 | 21176 |

Figure 5A:
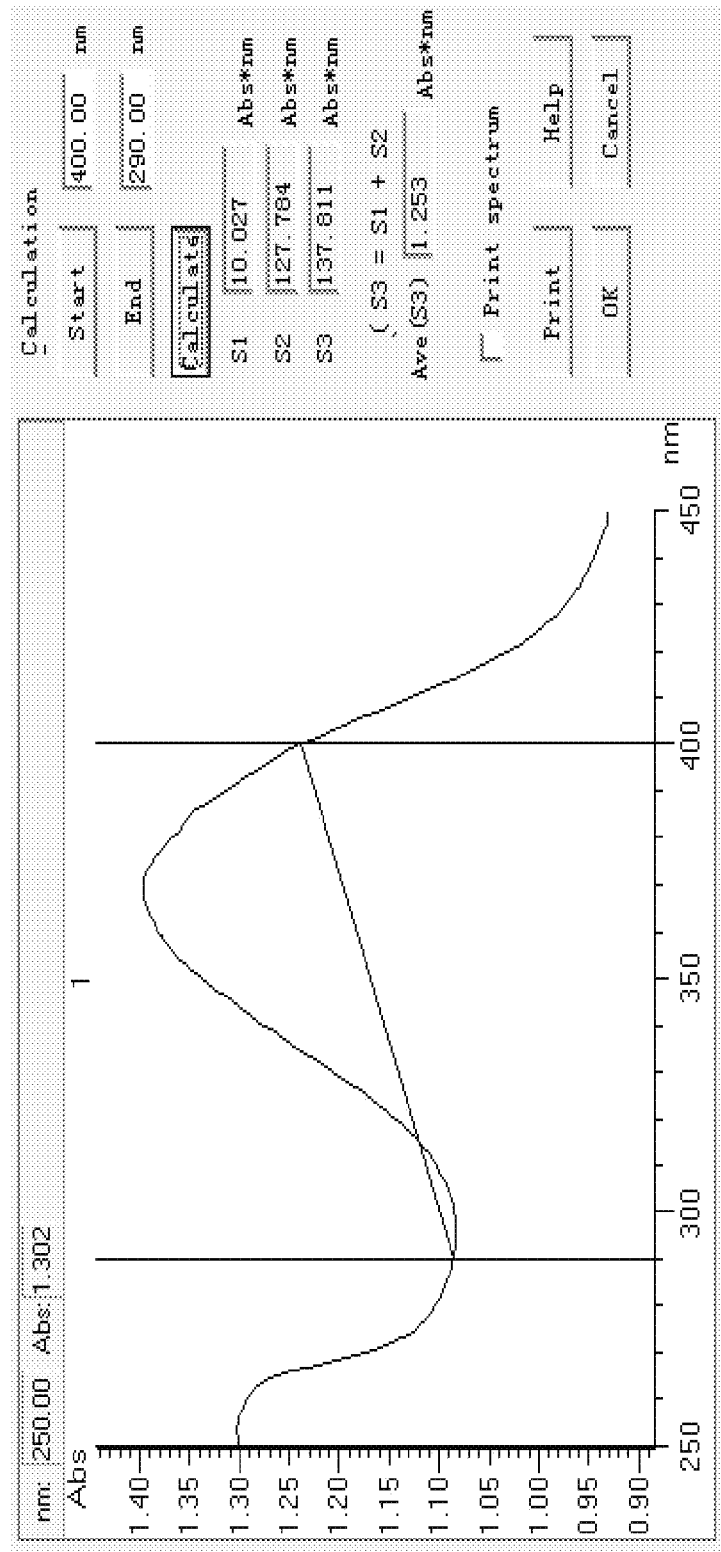
FIGS. 5A-5C are graphs depicting the data using a Critical Wavelength method to evaluate CDBA as a UVA protector.
Figure 5B:
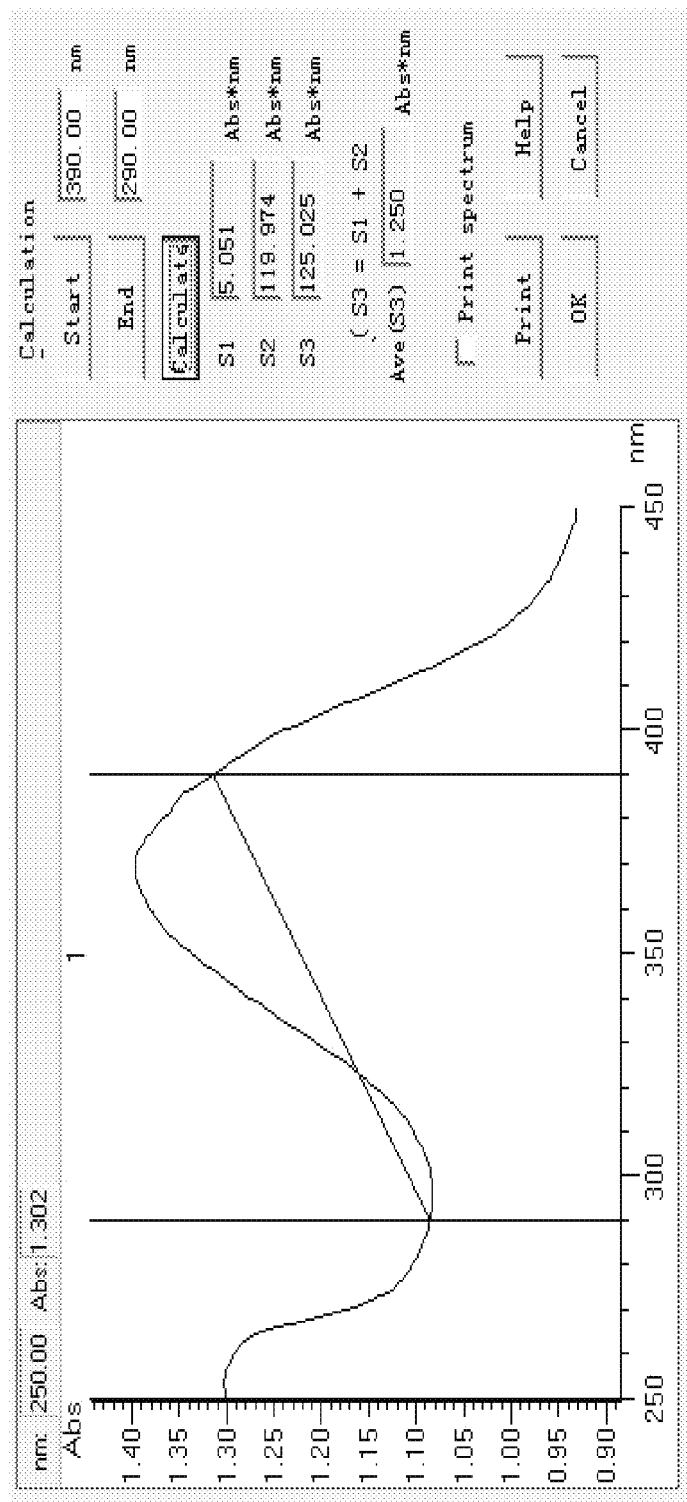
Figure 5C:
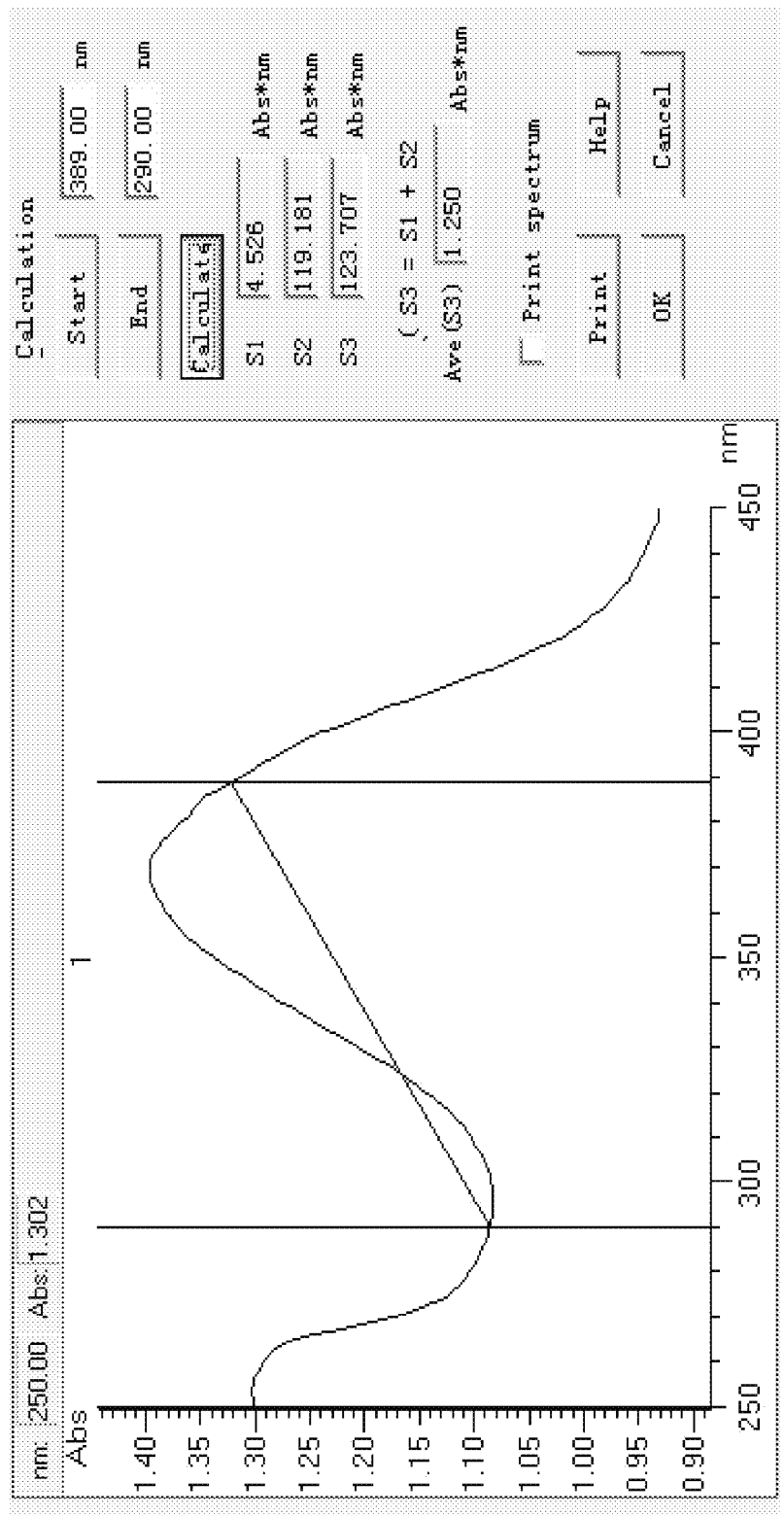

The critical wavelength method was then employed for evaluation of the molecule CDBA as a UVA protector. The results are shown in FIGS. 5A-5C, which are graphs depicting the data using the Critical Wavelength method to evaluate CDBA as a UVA protector. FIG. 5A shows an integrated area from 290 nm to 400 nm that was 137.811. Its 90% value was 124.030. FIG. 5B shows an integrated area from 290-390 of 125.025. FIG. 5C shows an integrated area from 290-389 of 123.707. Given this, the λc was determined to be between 389-390 nm. Furthermore, the results can be summarized as follows:

After 6 minutes of irradiation of UVA radiation (356 nm or 357 nm), 100% of the composition was isomeric.

After 8 minutes of irradiation of visible light radiation (442 nm or 443 nm), 99% of the molecules were isomeric.

After 3 hours of daylight irradiation, more than 90% of the molecules were isomeric, trans.

The results of the above experiments demonstrated that the various compounds had high (before irradiation of UVA) and medium (after irradiation of UVA) molar absorption coefficients. It was also observed that molecules having fatty groups have a higher molar absorption coefficient than aromatic compounds. In addition, it was observed that even though, as noted above, after 6 minutes' irradiation of UVA, PyB was more than 99% in the cis form (8 minutes for iQB), and after 8 minutes' irradiation of visible light, and more than 99% of the tested compounds were in the trans form, under irradiation of daylight, aromatic compounds were isomerized more slowly than fatty compounds.

It is noted that a λc≥370 nm is considered a 4 star product. Thus, the above class of compositions clearly offer good UVA protection.

EXAMPLE 15

Phototoxicity of various azo-compounds was examined. The compound used was that of 4-cholesterocarbonyl-4'-(N,N-diethyl aminebutyloxyl)azobenzene (CDBA) lipid, Formula XVI:

The UV source for the in vivo testing involved a 400 W high-pressure mercury lamp (LCE-9, Zhengzhou, China) with a filter transmitting the wavelength between 320-380 nm. Four test sites (4 cm²) were selected on the back of the rats. The sites were located between the breast and scapulae and lateral to the midline. The test product was applied at the amount of 20 ul/cm² (0.06 mg CDBA) and spread uniformly over one test site using a finger cot. The product was allowed to dry for 15 min before starting the UV exposure. On each test site, four squares (1 cm×1 cm) were defined, on an unprotected skin area of the rat dorsal and on a sunscreen-protected area. The skin was kept at a distance of 15 cm from the light source and the time of illumination was 5 hours on the test sites.

Figure 6:
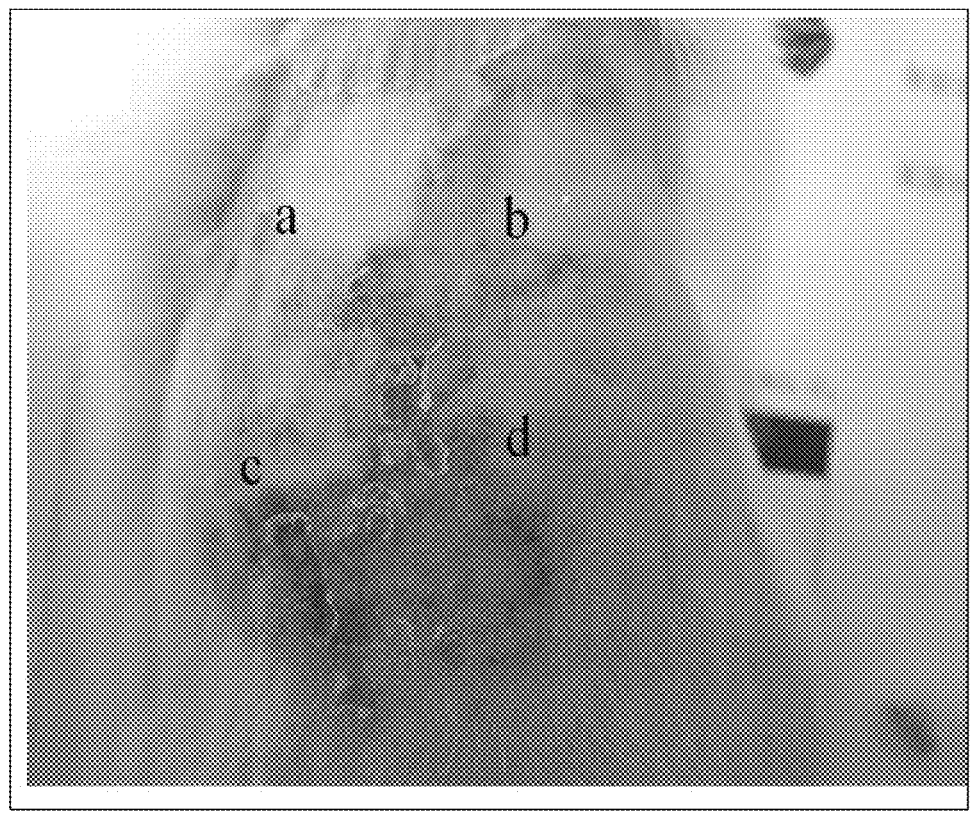
FIG. 6 is a photo depicting the effectiveness of various azo compounds at blocking UV irradiation.

The results are shown in FIG. 6, which is a photo showing a rat back shaved to the skin and treated with a) avobenzone in liposome; b) the above noted azo compound in liposome; c) liposome (PC+Chol); and d) avobenzone, three days after UV irradiation for 5 h. As can be seen in the photograph, structurally similar azo compound effectively protected skin from UV irradiation while causing no adverse effect including allergy.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For

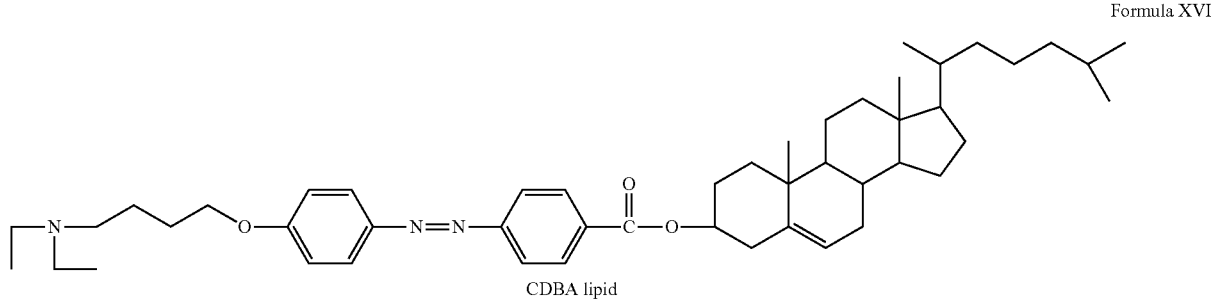 [SMILES: CCN(CC)CCCCOc1ccc(N=Nc2ccc(C(=O)OC3CCC4(C)C(=CCC5C4CCC4(C)C(C(C)CCCC(C)C)CCC54)C3)cc2)cc1]

Formula XVI

CDBA lipid

What is claimed is:

1. A molecule comprising an azobenzene group attached to a heterocycle group and a cholesterol group wherein the azobenzene group has the formula of Formula I:

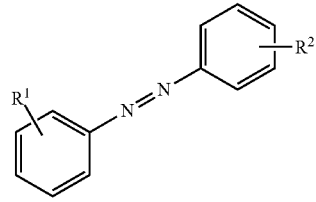

Formula I wherein R1 comprises a heterocycle group or a substituted variant thereof and wherein R2 comprises a cholesterol group or a substituted variant thereof, and, wherein the heterocycle group is selected from Formula II, VI, VII, VIII, or IX:

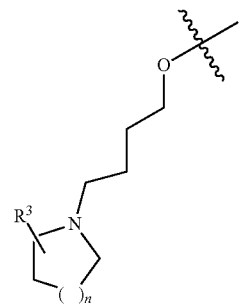

Formula II wherein n=1 or 2, and wherein R3 is either no substitution or a phenyl group,

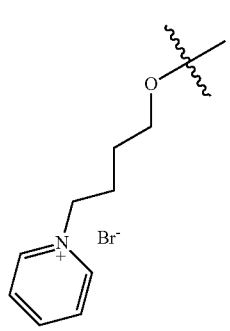

VI

-continued

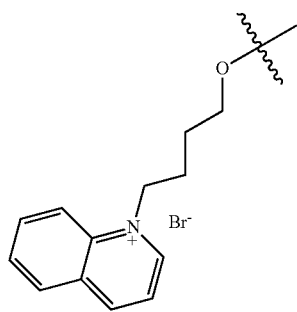
VII

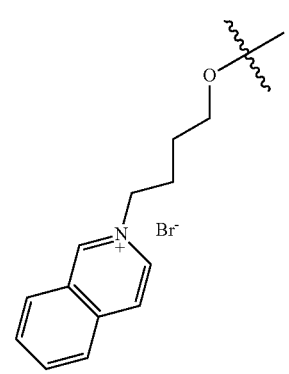
VIII

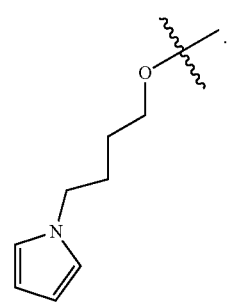
IX

2. The molecule of claim 1, wherein the heterocycle is connected to the structure of Formula I via an alkoxy member.

3. The molecule of claim 2, wherein the alkoxy member comprises 1, 2, 3, 4, 5, 6, 7, or 8 carbons.

4. The molecule of claim 3, wherein the heterocycle group comprises the structure shown in Formula II:

Formula II

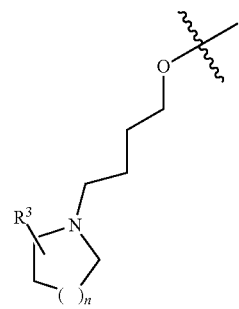

wherein n=1 or 2, and wherein R3 is either no substitution or a phenyl group.

5. The molecule of claim 4, wherein R3 can be in the ortho-position or meso-position to the nitrogen.

6. The molecule of claim 1, wherein the cholesterol group is selected from the group consisting of:

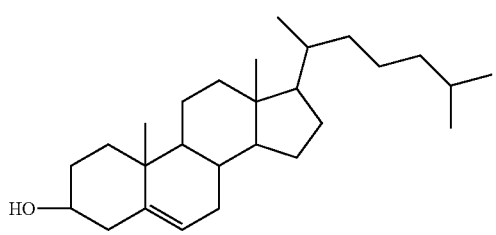
X

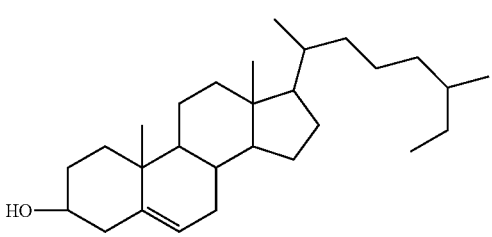
XI

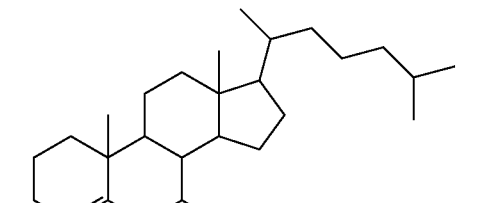
XII

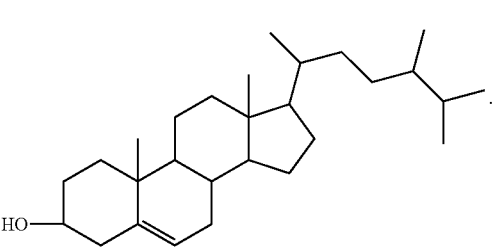
XIII

7. The molecule of claim 5, wherein the cholesterol group comprises the structure of Formula III:

Formula III

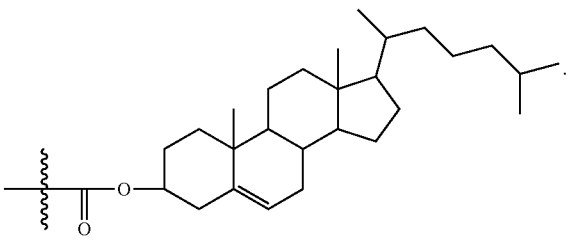

8. The molecule of claim 1, wherein the molecule comprises the structure of Formula IV:

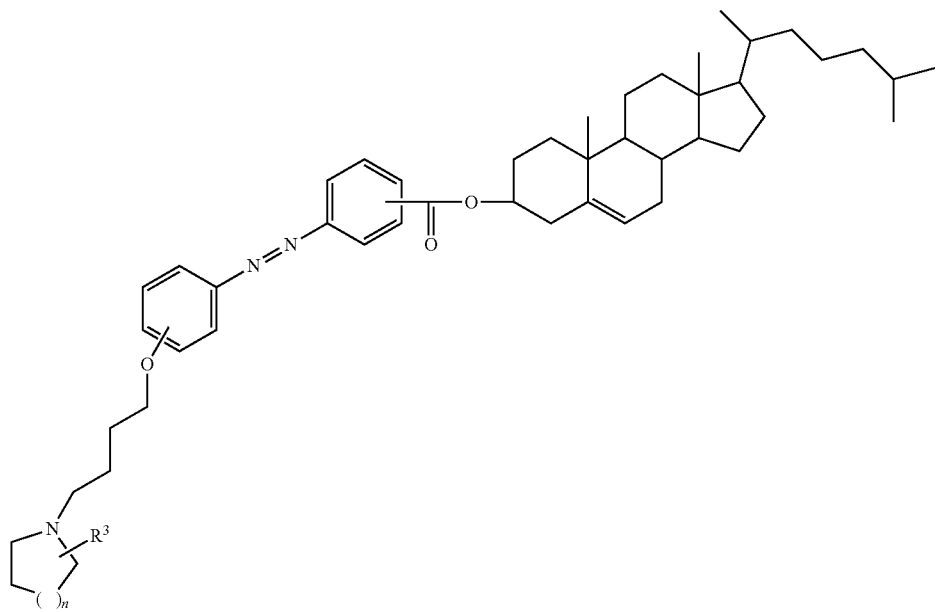

Formula IV wherein n=1 or 2 and wherein R3 is either no substitution or a phenyl group.

9. The molecule of claim 1, wherein the molecule comprises the structure of Formula V:

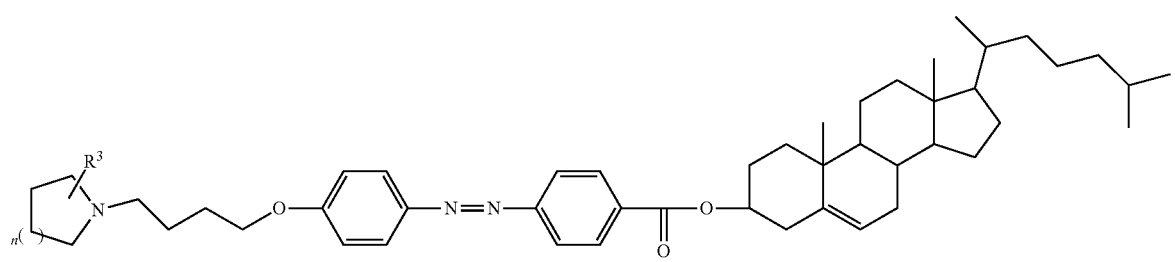

Formula V wherein n=1 or 2, and wherein R3 is either no substitution or a phenyl group, and wherein when the when R3 is a phenyl group, the phenyl is in the ortho or meso-position to the nitrogen in the heterocycle.

* * * * *

UNITED STATES PATENT AND TRADEMARK OFFICE
CERTIFICATE OF CORRECTION

PATENT NO.       : 8,835,643 B2                                   Page 1 of 3
APPLICATION NO.  : 13/878947
DATED            : September 16, 2014
INVENTOR(S)      : Wang It is certified that error appears in the above-identified patent and that said Letters Patent is hereby corrected as shown below:

On the Title Page, item (56), under "OTHER PUBLICATIONS", in Column 2, Line 33, delete "suncreens"" and insert -- sunscreens" --, therefor.

In the Specification

In Columns 5 & 6, in Formula IV, delete " 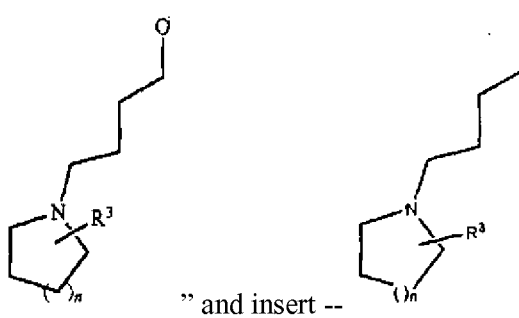 " and insert -- -- therefor.

In Columns 7 & 8, in Formula V, delete " 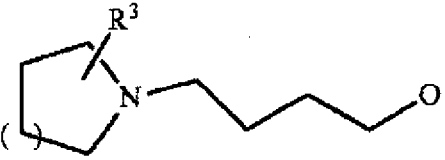 " and insert -- 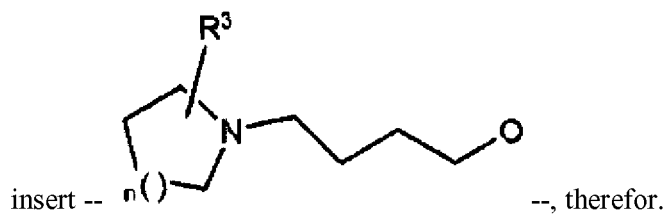 --, therefor.

In Column 11, Line 55, delete "any to" and insert -- any two --, therefor.

In Column 11, Line 60, delete "any to" and insert -- any two --, therefor.

Signed and Sealed this
Tenth Day of March, 2015

Michelle K. Lee
*Deputy Director of the United States Patent and Trademark Office*

In Column 12, Lines 2-3, delete "any to" and insert -- any two --, therefor.

In Column 12, Line 8, delete "any to" and insert -- any two --, therefor.

In Column 12, Line 45, delete "any to" and insert -- any two --, therefor.

In Columns 19 & 20, in Formula V, delete " 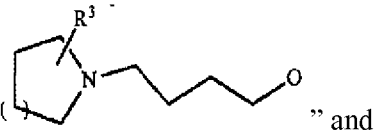 " and insert -- 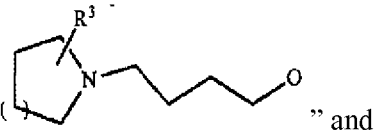 --, therefor.

In Columns 19 & 20, in Formula V, delete " 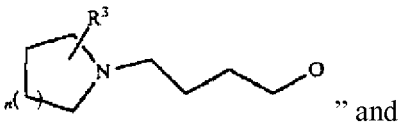 " and insert -- 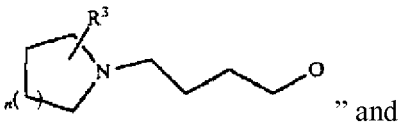 --, therefor.

In Column 16, Line 27, delete "NaHCO3" and insert -- $NaHCO_3$ --, therefor.

In Column 17, Line 8, delete "CDCl3," and insert -- $CDCl_3$, --, therefor.

In Columns 17 & 18, in Formula V, delete " 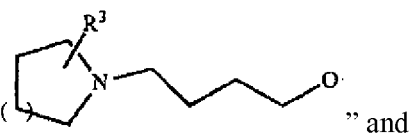 " and insert -- 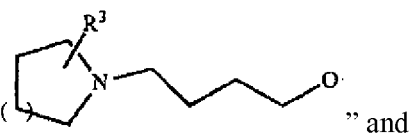 --, therefor.

In Column 25, Lines 2-3, delete "at least one and one or more" and insert -- "at least one" and "one or more" --, therefor.

In the Claims

In Column 26, Line 34, in Claim 1, delete "Formula II" and insert -- Formula II, --, therefor.

CERTIFICATE OF CORRECTION (continued)

U.S. Pat. No. 8,835,643 B2

In Columns 29 & 30, in Formula V, in Claim 9, delete " 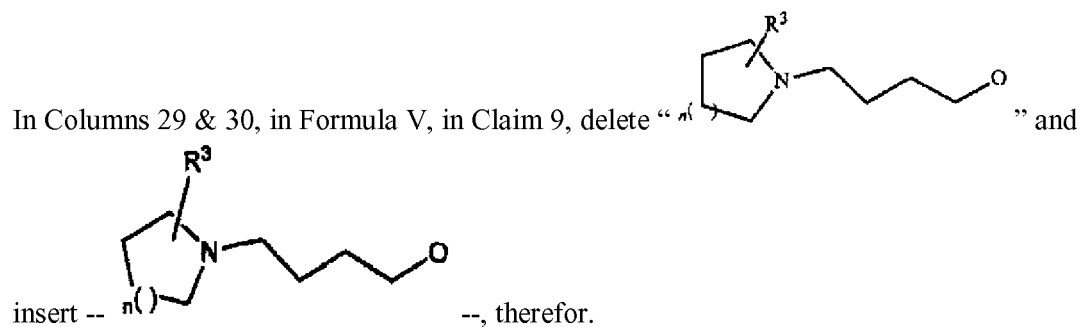 " and insert -- -- , therefor.

In Column 29, Line 50, in Claim 9, delete "when the when" and insert -- when the --, therefor.